(12) United States Patent
Liu et al.

(10) Patent No.: US 12,131,809 B2
(45) Date of Patent: Oct. 29, 2024

(54) CHARACTER ACQUISITION, PAGE PROCESSING AND KNOWLEDGE GRAPH CONSTRUCTION METHOD AND DEVICE, MEDIUM

(71) Applicant: BOE TECHNOLOGY GROUP CO., LTD., Beijing (CN)

(72) Inventors: Nan Liu, Beijing (CN); Chuan Wang, Beijing (CN); Xinyu Miao, Beijing (CN); Yiming Lei, Beijing (CN); Hong Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 983 days.

(21) Appl. No.: 16/982,185

(22) PCT Filed: Nov. 25, 2019

(86) PCT No.: PCT/CN2019/120634
§ 371 (c)(1),
(2) Date: Sep. 18, 2020

(87) PCT Pub. No.: WO2021/102632
PCT Pub. Date: Jun. 3, 2021

(65) Prior Publication Data
US 2022/0415456 A1     Dec. 29, 2022

(51) Int. Cl.
*G16H 10/40*     (2018.01)
*G06F 18/22*     (2023.01)
*G06N 5/022*     (2023.01)

(52) U.S. Cl.
CPC ............. *G16H 10/40* (2018.01); *G06F 18/22* (2023.01); *G06N 5/022* (2013.01)

(58) Field of Classification Search
CPC ........ G16H 10/40; G06F 18/22; G06N 5/022; G06V 30/26; G06V 30/412
See application file for complete search history.

(56) References Cited

U.S. PATENT DOCUMENTS

| | | | |
|---|---|---|---|
| 2006/0210171 A1 | 9/2006 | Yasunaga | |
| 2011/0060584 A1* | 3/2011 | Ferrucci | G06F 40/232 |
| | | | 704/9 |
| 2012/0065997 A1 | 3/2012 | Farooq et al. | |

FOREIGN PATENT DOCUMENTS

| | | |
|---|---|---|
| CN | 104268814 | 7/2015 |
| CN | 108073569 | 5/2018 |

(Continued)

OTHER PUBLICATIONS

Kanjanawattana, S. and Kimura, M., 2017. Novel ontologies-based optical character recognition-error correction cooperating with graph component extraction. BRAIN. Broad Research in Artificial Intelligence and Neuroscience, 7(4), pp. 69-83.*

(Continued)

*Primary Examiner* — Zhitong Chen
(74) *Attorney, Agent, or Firm* — Leason Ellis LLP

(57) ABSTRACT

A method and a device for acquiring character information in a picture, a non-transitory storage medium, a page processing method, and a knowledge graph construction method are disclosed. The method for acquiring character information in a picture includes: acquiring a picture and extracting at least one piece of character information in the picture; and checking-and-correcting the at least one piece of character information based on a knowledge graph.

15 Claims, 10 Drawing Sheets

(56) References Cited

FOREIGN PATENT DOCUMENTS

| CN | 109284396 | 1/2019 |
|---|---|---|
| CN | 109918640 | 6/2019 |
| CN | 110059195 | 7/2019 |
| JP | H0528323 A | 2/1993 |
| JP | 2008293109 A | 12/2008 |
| KR | 20150129922 A | 11/2015 |

OTHER PUBLICATIONS

Yehia, E., Boshnak, H., AbdelGaber, S., Abdo, A. and Elzanfaly, D.S., 2019. Ontology-based clinical information extraction from physician's free-text notes. Journal of biomedical informatics, 98, p. 103276.*

Engy Yehia et al., "Ontology-based clinical information extraction from physician's free-text notes", Journal of Biomedical Informatics, 2019, vol. 98. 14 pages.

Partial Supplementary European Search Report for corresponding European Application No. 19945445.5, dated Nov. 10, 2022.

Office Action in Japanese Patent Application No. 2022-504256, mailed Nov. 6, 2023, 53 pages.

* cited by examiner

| 11 | Platelet Ratio Volume | PCT | 0.310 | | % | 0.108-0.282 |
| 12 | Mean Platelet Volume | MPV | 9.3 | | fL | 9.4-12.5 |
| 13 | Platelet Distribution Width | PDW | 10.0 | | fL | 15.5-18.1 |
| 14 | Large Platelet Ratio | P-LCR | 19.3 | | % | 13-43 |
| 15 | Neutrophil Percentage | NEUT% | 53.80 | | % | 45.00-75.00 |
| 16 | Lymphocyte Percentage | LYMPH% | 35.90 | | % | 20-50 |

FIG. 7A

| 11 | Platelet Ratio Volume | PCT | 0.310 | | % | 0.108-0.282 |
| 12 | Mean Plat  Volume | MPV | 9.3 | | fL | 9.4-12.5 |
| 13 | Platelet Distribution Width | PDW | 10.0 | | fL | 15.5-18.1 |
| 14 | Large Platelet  atio | P-LCR | 19.3 | | % | 13-43 |
| 15 | Neutrophil Percentage | NEUT% | 53.80 | | % | 45.00-75.00 |
| 16 | Lymphocyte    tage | LYMPH% | 35.90 | | % | 20-50 |

FIG. 7B

```
"AL035": {
    "recordId": "AL035",
    "name": 'Platelet Ratio Volume',
    "recordDetail": {
        "value": "0.310",
        "unit": "%",
        "normalRange": "0.108-0.282",
        "hit": 'Normal',
        "state": 4,
        "recordType": "value"
    },
    "abbrEn": "PCT",
    "recordType": "value",
    "belongPanel": "AL0011"
},
"AL039": {
    "recordId": "AL039",
    "name": 'Mean Platelet Volume',
```
```
"AL036": {
    "recordId": "AL036",
    "name": 'Platelet Distribution Width',
```
```
"AL040": {
    "recordId": "AL040",
    "name": 'Large Platelet Ratio',
```
```
"AL025": {
    "recordId": "AL025",
    "name": 'Neutrophil Percentage',
```
```
"AL023": {
    "recordId": "AL023",
    "name": 'Lymphocyte Percentage',
```

FIG. 7C

CHARACTER ACQUISITION, PAGE PROCESSING AND KNOWLEDGE GRAPH CONSTRUCTION METHOD AND DEVICE, MEDIUM

CROSS-REFERENCE TO RELATED PATENT APPLICATIONS

This application is a U.S. National Stage Application under 35 U.S.C. § 371 of International Patent Application No. PCT/CN2019/120634, filed Nov. 25, 2019, which is incorporated by reference in its entirety.

TECHNICAL FIELD

Embodiments of the present disclosure relate to a method and a device for acquiring character information in a picture, a storage medium, a page processing method, and a knowledge graph construction method.

BACKGROUND

A patient (or a physical examinee) will go through a lot of medical examinations and tests to confirm whether the body is healthy, and the medical examination and test result is used as auxiliary information for the doctor to make a diagnosis. However, after obtaining paper documents (test reports, prescriptions, medical records, medical examination reports, etc.), patients may throw away paper documents or store them in a corner at home. Therefore, a preservation rate of the patient's historical medical examination and test data is low, and it is difficult to reuse it. In addition, paper documents and their images are unstructured data, which is not easy to check and manage.

Optical character recognition (OCR) technology can directly convert a text content on pictures and photos into editable text. For example, OCR technology can extract text content from pictures in JPG, PNG, GIF, BMP, DOC and other formats.

SUMMARY

At least one embodiment of the present disclosure provides a method for acquiring character information in a picture, which comprises: acquiring a picture and extracting at least one piece of character information in the picture; and checking-and-correcting the at least one piece of character information based on a knowledge graph.

For example, in at least one example of the method for acquiring character information in a picture, the checking-and-correcting the at least one piece of character information based on a knowledge graph comprises: identifying character information having an error in the at least one piece of character information based on the knowledge graph; and correcting the character information having an error based on the knowledge graph.

For example, in at least one example of the method for acquiring character information in a picture, the at least one piece of character information comprises a plurality of pieces of character information. The identifying character information having an error in the at least one piece of character information based on the knowledge graph comprises: obtaining a plurality of entities respectively based on the plurality of pieces of character information in the picture, and selecting an entity from the plurality of entities as a to-be-checked-and-corrected entity for a process of determining whether character information corresponding to the to-be-checked-and-corrected entity has an error; and determining whether the character information corresponding to the to-be-checked-and-corrected entity has an error according to a hierarchical structure of the knowledge graph, and identifying the character information corresponding to the to-be-checked-and-corrected entity as the character information having an error when the character information corresponding to the to-be-checked-and-corrected entity has an error.

For example, in at least one example of the method for acquiring character information in a picture, the determining whether the character information corresponding to the to-be-checked-and-corrected entity has an error according to a hierarchical structure of the knowledge graph comprises: grading the plurality of entities according to the hierarchical structure of the knowledge graph; determining a level of the to-be-checked-and-corrected entity in the hierarchical structure of the knowledge graph; calculating a similarity between the to-be-checked-and-corrected entity and each entity that is at a same level and has a same relationship as the to-be-checked-and-corrected entity in the knowledge graph, to obtain a plurality of entity similarities related to the to-be-checked-and-corrected entity; and when a maximum value of the plurality of entity similarities is smaller than a predetermined entity similarity threshold, determining that the to-be-checked-and-corrected entity is a to-be-checked-and-corrected entity having an error and that the character information corresponding to the to-be-checked-and-corrected entity has an error.

For example, in at least one example of the method for acquiring character information in a picture, using a minimum edit distance algorithm to obtain the similarity between the to-be-checked-and-corrected entity and each entity that is at the same level and has the same relationship as the to-be-checked-and-corrected entity in the knowledge graph.

For example, in at least one example of the method for acquiring character information in a picture, the correcting the character information having an error based on the knowledge graph comprises: determining a number of all entities that are at the same level and have the same relationship as the to-be-checked-and-corrected entity in the knowledge graph, to obtain an entity number. When the entity number is equal to 1, directly replacing character information corresponding to the to-be-checked-and-corrected entity having an error with character information corresponding to the entity that is at the same level and has the same relationship as the to-be-checked-and-corrected entity in the knowledge graph; or calculating a probability that the entity that is at the same level and has the same relationship as the to-be-checked-and-corrected entity is the to-be-checked-and-corrected entity having an error, to obtain an entity probability, and when the entity probability is larger than a predetermined entity probability, replacing character information corresponding to the to-be-checked-and-corrected entity having an error with character information corresponding to the entity that is at the same level and has the same relationship as the to-be-checked-and-corrected entity. When the entity number is larger than 1, performing a following method comprising: determining at least two candidate entities based on the plurality of entity similarities; calculating a probability that each of the at least two candidate entities is the to-be-checked-and-corrected entity having an error, to obtain a candidate probability for the each of the at least two candidate entities; and replacing character information corresponding to the to-be-checked-and-corrected entity having an error with character information corresponding to a candidate entity corresponding to a maximum candidate probability.

For example, in at least one example of the method for acquiring character information in a picture, the determining at least two candidate entities based on the plurality of entity similarities comprises: sorting all entities that are at the same level and have the same relationship as the to-be-checked-and-corrected entity in the knowledge graph based on the plurality of entity similarities in a descending order, selecting a predetermined number of entities at a beginning of the sequence as the at least two candidate entities; or sorting all entities that are at the same level and have the same relationship as the to-be-checked-and-corrected entity in the knowledge graph based on the plurality of entity similarities in an ascending order, and selecting a predetermined number of entities at an end of the sequence as the at least two candidate entities.

For example, in at least one example of the method for acquiring character information in a picture, wherein the calculating a probability that each of the at least two candidate entities is the to-be-checked-and-corrected entity having an error comprises: determining whether the to-be-checked-and-corrected entity comprises a next-lower-level to-be-checked-and-corrected entity, to obtain a first determination result, wherein the next-lower-level to-be-checked-and-corrected entity is all entities that are subordinate to the to-be-checked-and-corrected entity and at a next lower level of the to-be-checked-and-corrected entity; determining whether the to-be-checked-and-corrected entity corresponds to a relevant to-be-checked-and-corrected entity, to obtain a second determination result, wherein the relevant to-be-checked-and-corrected entity is all entities, that are at the same level as the to-be-checked-and-corrected entity in the hierarchical structure of the knowledge graph, related to the to-be-checked-and-corrected entity, and have a different relationship with an entity at a next higher level to which the to-be-checked-and-corrected entity is subordinate; and selecting a method for calculating the probability that the each of the at least two candidate entities is the to-be-checked-and-corrected entity having an error, based on the first determination result and the second determination result. The first determination result is a first determination sub-result when determining that the to-be-checked-and-corrected entity comprises the next-lower-level to-be-checked-and-corrected entity, or a second determination sub-result when determining that the to-be-checked-and-corrected entity does not comprise the next-lower-level to-be-checked-and-corrected entity; and the second determination result is a third determination sub-result when determining that the to-be-checked-and-corrected entity corresponds to the relevant to-be-checked-and-corrected entity or a fourth determination sub-result when determining that the to-be-checked-and-corrected entity does not correspond to the relevant to-be-checked-and-corrected entity.

For example, in at least one example of the method for acquiring character information in a picture, the selecting a method for calculating the probability that the each of the at least two candidate entities is the to-be-checked-and-corrected entity having an error, based on the first determination result and the second determination result comprises: when the first determination result is the first determination sub-result and the second determination result is the third determination sub-result, calculating the candidate probability for the each of the at least two candidate entities using at least one of the next-lower-level to-be-checked-and-corrected entity and the relevant to-be-checked-and-corrected entity; when the first determination result is the second determination sub-result and the second determination result is the third determination sub-result, calculating the candidate probability for the each of the at least two candidate entities using the relevant to-be-checked-and-corrected entity; when the first determination result is the first determination sub-result and the second determination result is the fourth determination sub-result, calculating the candidate probability for the each of the at least two candidate entities using the next-lower-level to-be-checked-and-corrected entity; and when the first determination result is the second determination sub-result and the second determination result is the fourth determination sub-result, taking the entity similarity for the each of the at least two candidate entities as the probability for the each of the at least two candidate entities being the to-be-checked-and-corrected entity having an error.

For example, in at least one example of the method for acquiring character information in a picture, the calculating the candidate probability for the each of the at least two candidate entities using the relevant to-be-checked-and-corrected entity comprises: obtaining the relevant to-be-checked-and-corrected entity corresponding to the to-be-checked-and-corrected entity. For each entity in the relevant to-be-checked-and-corrected entity, performing a method comprising: obtaining a relevant candidate entity, wherein the relevant candidate entity is at a same level as the each of the at least two candidate entities in the hierarchical structure of the knowledge graph, is related to the each of the at least two candidate entities, and has a relationship to the each of the at least two candidate entities equal to a relationship between the each entity in the relevant to-be-checked-and-corrected entity and the to-be-checked-and-corrected entity; and calculating a similarity between the each entity in the relevant to-be-checked-and-corrected entity and the relevant candidate entity. Obtaining a relevant similarity for the each of the at least two candidate entities based on the similarity between the each entity in the relevant to-be-checked-and-corrected entity and the relevant candidate entity; and obtaining the candidate probability for the each of the at least two candidate entities based on the relevant similarity and the entity similarity for the each of the at least two candidate entities.

For example, in at least one example of the method for acquiring character information in a picture, the obtaining a relevant similarity for the each of the at least two candidate entities based on the similarity between the each entity in the relevant to-be-checked-and-corrected entity and the relevant candidate entity comprises: determining an entity number of entities in the relevant to-be-checked-and-corrected entity; when the entity number of entities in the relevant to-be-checked-and-corrected entity is equal to 1, taking the similarity between the each entity in the relevant to-be-checked-and-corrected entity and the relevant candidate entity as the relevant similarity for the each of the at least two candidate entities; when the entity number of entities in the relevant to-be-checked-and-corrected entity is larger than 1, taking a weighted sum of a plurality of similarities between the entities in the relevant to-be-checked-and-corrected entity and the relevant candidate entity as the relevant similarity for the each of the at least two candidate entities. The obtaining the candidate probability for the each of the at least two candidate entities based on the relevant similarity and the entity similarity for the each of the at least two candidate entities comprises: taking a weighted sum of the relevant similarity and the entity similarity for the each of the at least two candidate entities as the candidate probability for the each of the at least two candidate entities.

For example, in at least one example of the method for acquiring character information in a picture, the calculating the candidate probability for the each of the at least two candidate entities using the next-lower-level to-be-checked-and-corrected entity comprises: obtaining the lower-level to-be-checked-and-corrected entity comprised by the to-be-checked-and-corrected entity; dividing the next-lower-level to-be-checked-and-corrected entity into at least one next-lower-level to-be-checked-and-corrected entity group based on a relationship between the to-be-checked-and-corrected entity and each entity of the next-lower-level to-be-checked-and-corrected entity. For each of the at least one next-lower-level to-be-checked-and-corrected entity group, performing a method comprising: obtaining a lower-level candidate entity group, wherein the lower-level candidate entity group comprises all entities subordinate to the each of the at least two candidate entities, and have a relationship with the each of the at least two candidate entities equal to a relationship between each of the entities in the next-lower-level to-be-checked-and-corrected entity group and the to-be-checked-and-corrected entity; calculating a similarity between each group of the at least one next-lower-level to-be-checked-and-corrected entity group and the lower-level candidate entity group, to obtain at least one group similarity corresponding to the at least one next-lower-level to-be-checked-and-corrected entity group. Obtaining a lower-level similarity for the each of the at least two candidate entities based on the at least one group similarity; and calculating the candidate probability for the each of the at least two candidate entities based on the lower-level similarity and the entity similarity for the each of the at least two candidate entities.

For example, in at least one example of the method for acquiring character information in a picture, wherein obtaining at least one group similarity corresponding to the at least one next-lower-level to-be-checked-and-corrected entity group comprises: obtaining a maximum similarity for each of the plurality of entities in the each group of the at least one next-lower-level to-be-checked-and-corrected entity group, to obtain a plurality of maximum similarities for the plurality of entities in the each group of the at least one next-lower-level to-be-checked-and-corrected entity group, wherein the maximum similarity is a similarity has a maximum value among similarities between the each of the plurality of entities in the each group of the at least one next-lower-level to-be-checked-and-corrected entity group and all entities in the lower-level candidate entity group, and obtaining at least one group similarity corresponding to the at least one next-lower-level to-be-checked-and-corrected entity group based on the plurality of maximum similarities. The obtaining at least one group similarity corresponding to the at least one next-lower-level to-be-checked-and-corrected entity group based on the plurality of maximum similarities comprises: taking a weighted sum of the plurality of maximum similarities as the at least one group similarity corresponding to the at least one next-lower-level to-be-checked-and-corrected entity group.

For example, in at least one example of the method for acquiring character information in a picture, the obtaining a lower-level similarity for the each of the at least two candidate entities based on the at least one group similarity comprises: determining a number of the next-lower-level to-be-checked-and-corrected entity groups comprised by the next-lower-level to-be-checked-and-corrected entity; when the number of lower-level to-be-checked-and-corrected entity groups is equal to 1, taking the group similarity for the next-lower-level to-be-checked-and-corrected entity group comprised by the next-lower-level to-be-checked-and-corrected entity as the lower-level similarity for the each of the at least two candidate entities; when the number of lower-level to-be-checked-and-corrected entity groups is larger than 1, taking a weighted sum of a plurality of group similarities for the next-lower-level to-be-checked-and-corrected entity groups comprised by the next-lower-level to-be-checked-and-corrected entity as the lower-level similarity for each of the at least two candidate entities. The calculating the candidate probability for the each of the at least two candidate entities based on the lower-level similarity and the entity similarity for the each of the at least two candidate entities comprises: taking a product of the lower-level similarity and the entity similarity for the each of the at least two candidate entities as the candidate probability for the each of the at least two candidate entities.

For example, in at least one example of the method for acquiring character information in a picture, the calculating the candidate probability for the each of the at least two candidate entities using the next-lower-level to-be-checked-and-corrected entity and the relevant to-be-checked-and-corrected entity comprises: obtaining the relevant to-be-checked-and-corrected entity corresponding to the to-be-checked-and-corrected entity; for each entity in the relevant to-be-checked-and-corrected entity, performing a method comprising: obtaining a relevant candidate entity, wherein the relevant candidate entity is at a same level as the each of the at least two candidate entities in the hierarchical structure of the knowledge graph, is related to the each of the at least two candidate entities, and has a relationship to the each of the at least two candidate entities equal to a relationship between the each entity in the relevant to-be-checked-and-corrected entity and the to-be-checked-and-corrected entity, and calculating a similarity between the each entity in the relevant to-be-checked-and-corrected entity and the relevant candidate entity; obtaining a relevant similarity for the each of the at least two candidate entities based on the similarity between the each entity in the relevant to-be-checked-and-corrected entity and the relevant candidate entity; obtaining the lower-level to-be-checked-and-corrected entity comprised by the to-be-checked-and-corrected entity; dividing the next-lower-level to-be-checked-and-corrected entity into at least one next-lower-level to-be-checked-and-corrected entity group based on a relationship between the to-be-checked-and-corrected entity and each entity of the next-lower-level to-be-checked-and-corrected entity; for each of the at least one next-lower-level to-be-checked-and-corrected entity group, performing a method comprising: obtaining a lower-level candidate entity group, wherein the lower-level candidate entity group comprises all entities subordinate to the each of the at least two candidate entities, and have a relationship with the each of the at least two candidate entities equal to a relationship between each of the entities in the next-lower-level to-be-checked-and-corrected entity group and the to-be-checked-and-corrected entity, calculating a similarity between each group of the at least one next-lower-level to-be-checked-and-corrected entity group and the lower-level candidate entity group, to obtain at least one group similarity corresponding to the at least one next-lower-level to-be-checked-and-corrected entity group; obtaining a lower-level similarity for the each of the at least two candidate entities based on the at least one group similarity; and obtaining the candidate probability for each of the at least two candidate entities based on the relevant similarity, the lower-level similarity and the entity similarity for each of the at least two candidate entities At least one embodiment of the present disclosure further provides a device for acquiring character information in a picture, which comprises: a character information extraction device and a check-correction device. The character information extraction device is configured to acquire a picture and extract at least one piece of character information in the picture; and the check-correction device is configured to check and correct at least one piece of character information based on a knowledge graph.

At least one embodiment of the present disclosure further provides a device for acquiring character information in a picture, which comprises: a processor and a memory. The memory stores computer program instructions suitable to be executed by the processor. Upon the computer program instructions are executed by the processor, the processor is allowed to execute any method for acquiring character information in a picture provided by at least one embodiment of the present disclosure.

At least one embodiment of the present disclosure further provides a non-transitory storage medium, which comprising computer program instructions stored on the non-transitory storage medium. When the computer program instructions are executed by the a processor, a computer executes any method for acquiring character information in a picture provided by at least one embodiment of the present disclosure.

At least one embodiment of the present disclosure further provides a device for acquiring character information in a picture page processing method, which comprises: obtaining a picture of a page; and acquiring checked-and-corrected character information in the picture of the page by performing any method for acquiring character information in a picture provided by at least one embodiment of the present disclosure; and structuring the checked-and-corrected character information in the picture of the page to obtain a structured data combination.

For example, in at least one example of the page processing method, the page processing method further comprises: confirming that the picture of the page comprises a medical image based on a knowledge graph; and adding the medical image to the structured data combination.

For example, in at least one example of the page processing method, the confirming that the picture of the page comprises a medical image based on a knowledge graph comprises: determining that the picture of the page comprises a medical image based on that the character information, that is extracted from the picture of the page and is checked and corrected based on the knowledge graph comprises a text corresponding to a medical image.

For example, in at least one example of the page processing method, the page processing method further comprises: based on the knowledge graph and a plurality of entities corresponding to the checked-and-corrected character information, adding descriptions corresponding to the plurality of entities to the structured data combination.

At least one embodiment of the present disclosure further provides a method for constructing a knowledge graph, which comprises: obtaining a data structure of a medical knowledge graph; exporting corresponding entities at least from a medical image archiving and communication system and a laboratory information management system; performing entity alignment through aligning entities exported from the medical image archive and communication system with entities exported from the laboratory information management system, to obtain a plurality of entities after entity alignment; and filling the plurality of entities after entity alignment into the medical knowledge graph based on the data structure of the medical knowledge graph.

For example, in at least one example of the method for constructing a knowledge graph, the method for constructing a knowledge graph further comprises: obtaining sub-item descriptions for clinical examination sub-items related to a laboratory information management system, processing the sub-item descriptions, and filling processed sub-item descriptions to the medical knowledge graph.

For example, in at least one example of the method for constructing a knowledge graph, the method for constructing a knowledge graph further comprises: exporting corresponding entities from a hospital information system, performing entity alignment through aligning entities exported from the hospital information system and the plurality of entities after entity alignment, and filling entities exported from the hospital information system and aligned with the plurality of entities after entity alignment into the medical knowledge graph based on the data structure of the medical knowledge graph.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

FIG. 7A is a picture corresponding to a partial blood routine examination report;

FIG. 7B is a picture of the partial blood routine examination report illustrated in FIG. 7A after being contaminated;

FIG. 7C illustrates a result of acquiring character information in a picture of FIG. 7B by using a software program based on the method for acquiring character information in a picture provided by at least one embodiment of the present disclosure;

DETAILED DESCRIPTION

Figure 1:
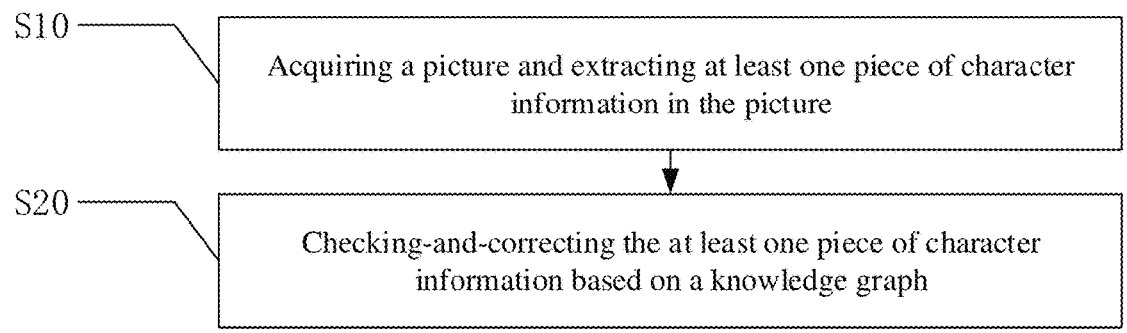
FIG. 1 is an exemplary flowchart of a method for acquiring character information in a picture provided by at least one embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

The inventors of the present disclosure have discovered in their research that although optical character recognition (OCR) technology can be used to extract text content from pictures, the text content extracted from pictures by OCR technology is only the characters themselves, and the extracted characters need to be integrated into a format that is consistent with the content of the picture and convenient for users to check according to a rule by parsing technology (for example, page parsing technology), so as to obtain information with specific meanings. For example, through ordinary optical character recognition technology and parsing technology, only the following operation can be performed: text content is extracted from the picture, and the text content in the picture is converted into a text format, thereby enabling the text content in the picture to be stored in the memory in text format (that is, the ordinary OCR technology and parsing technology only solve the problems of digitalizing and storing the electronic medical examination reports). However, a computer has a poor ability to understand the text content in the above text format, and the above content cannot be effectively retrieved and displayed (for example, displayed in a graphical user interface), so the patient's medical examination report cannot be effectively utilized.

In addition, the inventors of the present disclosure have also discovered in research that paper documents in the medical field (test reports, prescriptions, medical records, medical examination reports, etc.) involve uncommon words, uncommon terms, etc., and the characters of these uncommon words and uncommon terms are complex. Therefore, it can be difficult to recognize these uncommon words and uncommon terms by using an OCR module (i.e., conventional OCR module) trained by a conventional method. The inventors of the present disclosure have also discovered in research that a related medical OCR module has poor recognition performance for non-medical text. Therefore, from a synthetical point of view, conventional OCR modules and medical OCR modules have low accuracy in extracting character information from pictures corresponding to paper documents in the medical field. Because the accuracy of the extracted characters is closely related to the health of the patient, there is a need for a method to improve the accuracy of the extracted characters.

Knowledge graph is a cutting-edge research field of intelligent big data. It adapts to the development of the information age with its unique technical advantages. For example, the knowledge graph has the following advantages: incremental data schema design; good data integration capabilities; supported by standards such as existing resource description framework (RDF) and web ontology language (OWL); semantic search and knowledge reasoning capabilities. For example, a knowledge graph has better capabilities in querying complex related information, they can understand user intent from the semantic level, and they can have a strong ability to describe data. The knowledge graph can be used to describe various entities and concepts that exist in the real world. For example, a knowledge graph can be used to describe association between two entities. For example, "Yao Ming was born in Shanghai" involves two entities "Yao Ming" and "Shanghai" and the relationship "birthplace" between the above two entities.

In the medical field, with the development of regional health information and medical information systems, a large amount of medical data has been accumulated. How to extract information from these data, and manage, share and apply then is a key issue for promoting medical intelligence, and it is also the basis for medical knowledge retrieval, clinical diagnosis, medical quality management, electronic medical records and intelligent processing of health records. Medical knowledge graph is a method to realize smart medical treatment, which is beneficial to develop more efficient and accurate medical services. Based on the reasoning ability of knowledge graph, medical knowledge graph has two advantages of interpretability and stability. However, due to the following problems, the application scope of medical graph is relatively small (for example, only for knowledge inquiry and retrieval): the existing Chinese medical knowledge graph is small, the medical terminology in different regions is not consistent, and the construction of medical knowledge graph requires deep participation of medical experts, which leads to problems of low efficiency, many restrictions, and poor scalability Edit Distance refers to the minimum number of editing operations required to convert one string into another. Allowed editing operations include replacing one character with another character, inserting a character, and deleting a character. Generally speaking, the smaller the editing distance between two character strings, the greater the similarity between the two character strings.

For example, in a minimum edit distance algorithm, an edit distance between a character string consisting of i characters in a string (character string) A and a character string consisting of j characters in a string B can be represented by edit[i][j]; edit[i][j] represents an edit distance between a character string consisting of characters from the 0th character to the i-th character of the string A and a character string consisting of characters from the 0th character to the j-th character of the string B. For example, when the string A is "graph" and the string B is "grape", edit[5][5] represents an edit distance between the character string "graph" and the character string "grape"; edit[2][3] represents an edit distance between the character string "gr" and the character string "gra". For example, i and j can be larger than or equal to 1.

For example, the edit distance of the string A and the string B can also be presented as dis[i][j]. For example, dis[0][0] means that when both of the string A and the string B are empty, their edit distance is 0. Apparently, dis[0][j] is the case where the string A is empty and the string B has a length of j; at this time, the edit distance of the string A and the string B is j, that is, the minimum edit distance of converting the empty string into the string B by adding j characters is j. Similarly, dis[i][0] represents the minimum edit distance of converting the string A to empty by deleting i characters in the case where the length of the string A is i, the string B is empty, so the minimum edit distance of converting the string A to the string B is i.

Through the above description, the following dynamic programming equations can be obtained.

$$\text{edit } [i][j] = \begin{cases} 0 & i=0, j=0 \\ j & i=0, j>0 \\ i & i>0, j=0 \\ \min(\text{edit } [i-1][j]+1, \text{edit } [i][j-1]+1, \\ \quad \text{edit } [i-1][j-1]+\text{flag}) & i>0, j>0 \end{cases}$$

Where the effective number of replacement (flag) can be expressed by the following equation.

$$\text{flag} = \begin{cases} 0 & A[i] = B[j] \\ 1 & A[i] \neq B[j] \end{cases}$$

The min( ) function (that is, the function used to calculate the minimum value) in the above dynamic programming equation contains three expressions, namely, edit[i−1][j]+1, edit[i][j−1]+1 and edit[i−1][j−1]+flag, the above three expressions respectively represent an character insertion operation, a character deletion operation and a character replacement operation, which will be described below.

edit[i−1][j]+1 is equivalent to the case of inserting the last character in the string A after the last character of the string B. The insert character operation increases the edit distance by 1, and then the edit[i−1][j] is calculated to calculate edit[i−1][j]+1, and the above calculation is as part of the calculation of the edit distance edit[i][j];

edit[i][j−1]+1 is equivalent to the case of deleting the last character from the string B. The character deletion operation increases the edit distance by 1, and then edit[i] is calculated by calculating edit[i][j−1][j−1]+1, and the above calculation is as part of calculating the edit distance edit[i][j];

edit[i−1][j−1]+flag is equivalent to the case of replacing the last character of the string B with the last character of the string A. Here, the effective number of character replacements is recorded as a flag.

For example, the similarity for the two character strings can be obtained by calculating the edit distance of the two character strings with the minimum edit distance algorithm. For example, the similarity for the two character strings can be calculated through the following formula and using the edit distance of the two strings: S (A, B)=1−(DIS (A, B)/max (Len (A), Len (B)). Here, DIS (A, B) represents the edit distance of the string A and the string B, Len (A) and Len (B) represent the string length of the string A and the string length of the string B, max (Len(A), Len(B)) is equal to the maximum value of the length of the string A and the length of the string B.

At least one embodiment of the present disclosure provides a method and a device for acquiring character information in a picture, a non-transitory storage medium, a page processing method, and a knowledge graph construction method. The method for acquiring character information in a picture comprises: acquiring a picture and extracting at least one piece of character information in the picture; and checking-and-correcting the at least one piece of character information based on a knowledge graph. The method for acquiring character information in a picture can check-and-correct the at least one piece of character information based on a knowledge graph, such that the accuracy of acquired character information can be improved.

Non-limitative descriptions are given to a method for acquiring character information in a picture provided by at least an embodiment of the present disclosure in the following with reference to a plurality of examples or embodiments. As described in the following, in case of no conflict, different features in these specific examples or embodiments may be combined so as to obtain new examples or embodiments, and the new examples or embodiments are also fall within the scope of present disclosure.

FIG. 1 is an exemplary flowchart of a method for acquiring character information in a picture provided by at least one embodiment of the present disclosure. As illustrated in FIG. 1, the method for acquiring character information in a picture includes the following steps S10 and S20.

Step S10: acquiring a picture and extracting at least one piece of character information in the picture.

Step S20: checking-and-correcting the at least one piece of character information based on a knowledge graph.

In step S10, a specific method for acquiring a picture can be adopted according to actual application requirements, which is not specifically limited in at least one embodiment of the present disclosure. In an example, acquiring a picture may include acquiring (reading) a picture stored in the memory from the memory. In another example, acquiring a picture may include acquiring a picture remotely, for example, with an information sending-receiving device to receive the picture. For example, the information sending-receiving device may receive a picture from a client (for example, mobile phone mobile terminal or PC terminal).

For example, in step S10, the acquired picture may be a picture after picture preprocessing or a picture before picture preprocessing. For example, when the acquired picture is a picture before picture preprocessing, before extracting at least one piece of character information in the picture, the picture may be preprocessed. For example, picture preprocessing includes, but is not limited to, at least one of detection and extraction of the main area of the picture, picture correction, picture segmentation, text direction correction of the picture, picture binarization, and picture denoising.

For example, the detection and extraction of the main area of a picture includes detecting the main area (effective area, area containing useful information) of the above picture, and extracting the detected main area, in which the extracted main area serves as a picture for subsequent processing. For example, the main area of the picture may be detected by locating the area where the text exists in the picture (text detection), that is, finding the boundary box of the word or Word/Line-level. For example, in the detection and extraction of the main area of a picture, the user can confirm the detected main area before extraction (that is, manually select an effective area by the user) to improve the accuracy of the detection and extraction of the main area of the picture.

For example, picture correction (for example, keystone correction) is used to correct the distortion of pictures (for example, pictures taken by mobile phones). For example, gamma correction can be used to implement picture correction (e.g., keystone correction).

For example, picture segmentation is used to segment text (for example, text from a medical examination report) from a picture that contains a background (for example, a photo taken by an ordinary mobile phone), so as to improve the accuracy of the text (for example, character information) extracted from the picture. For example, text can be segmented from a picture containing a background by the following method.

First, horizontally project the picture to find the upper and lower limits of each line. Second, perform line cutting along the upper and lower limits of each line to obtain a plurality of lines. Third, for each line obtained by cutting, vertical projection is performed to find the left and right borders of each character. Fourth, individual characters are obtained by cutting along the left and right borders of each character. For example, horizontal projection is used to count the elements of each row of a picture (that is, counting along the horizontal direction). Then, a graph of a counting result may be drawn based on the result of the counting, thereby determining the starting point and ending point of each row along the column direction, that is, the upper and lower limits of each line. For example, the projection direction of the vertical projection is downward, which is used to count the number of elements in each column and the projection position of the elements in each column, thereby determining the left and right limits of each column.

For example, the following methods can be used to perform horizontal projection on a picture. First, a straight line (axis) extending in the vertical direction is set. Second, pixels on the picture are projected in a direction perpendicular to the straight line (axis) to project the picture on a straight line (axis), and after projection, a plurality of pixels on the picture correspond to a plurality of black dots on the straight line (axis). Third, the number of black dots of the pixels on the picture perpendicular to the vertical straight line are counted, and a sum of the numbers is taken as the value of the axis at the position. After the above horizontal projection is completed, cutting the picture based on projection can be performed. Specifically, after completing the above horizontal projection and obtaining relevant features, a cutting position (coordinates) of the picture is determined based on the above features, and the picture is cut based on the coordinates to obtain the target picture (for example, a picture of a single text obtained by dividing the picture). For example, vertically projecting a picture is similar to projecting a picture horizontally, except that a straight line extending in the vertical direction is set, and pixels on the picture are projected onto the straight line extending in the vertical direction.

The horizontal projection is exemplarily described in the following with reference to an example. For example, horizontal projection maybe achieved by the following method. First, a picture is binarized so that the text is black (for example, the pixel value corresponding to the text is Lb, for example, Lb=0), and the background is white (for example, the pixel value corresponding to the text is Lw, for example, Lw=255). Secondly, the following steps is performed for each row of the picture: sequentially determining whether the pixel value of each column is equal to Lb, and determining that the pixel in the row and column are very similar to text if the pixel value is equal to Lb; counting a number of the pixels similar to text in the row. Assuming that there are totally n pixels having a pixel value equal to Lb, the row from the first column to the nth column is set to black.

For example, the text direction correction of the picture is used to correct the tilt of the text in the image caused in the picture shooting process. For example, fast Fourier transformation technology can be used to correct the picture, and then, the corrected image is inversely transformed to obtain the text with the direction corrected.

For example, image binarization can be used to increase the contrast of the text. For example, the image binarization can be realized by the following method. First, a threshold is set. Then, for a plurality of pixels in the picture, a value (for example, the grayscale value of the pixel) of a pixel having a pixel value larger than or equal to the threshold is set to 1 (that is, make the pixel present white color), and a value of a pixel having a pixel value smaller than the threshold is set to 0 (that is, make the pixel present black color). For example, adaptive binarization can be used (each pixel uses a different threshold in the comparison process). For example, a two-dimensional matrix (that is, a matrix used to store the pixel values of the plurality of pixels of a picture) corresponding to the pixel values of the plurality of pixels of a picture may be converted into a vector, and then each pixel is compared to a threshold (that is, the adaptive threshold) calculated based on pixels which are before the each pixel and within a certain range.

For example, picture denoising is used to reduce picture noise to improve the accuracy of the text extracted from pictures. For example, after converting the received picture into a binary picture, there can be a lot of noise in the binary picture; for solving this problem, median filtering or mean filtering may be used to denoise the binary picture.

For example, the character information acquired from the picture may include a single piece of character information or a plurality of pieces of character information. For example, each piece of character information includes a single character or a character string. For example, the character information may be text information or symbol information. For example, the symbol information may be an ascending arrow symbol, a descending arrow symbol, or the like.

Figure 2A:
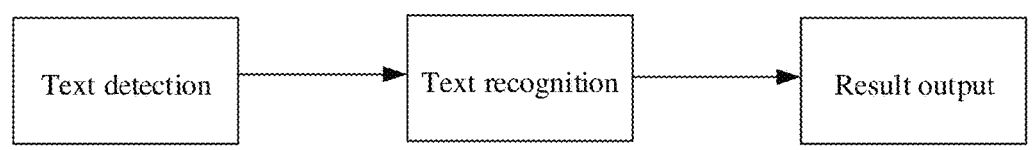
FIG. 2A is a schematic diagram illustrating a process of extracting at least one piece of character information included in a picture with optical character recognition technology.

For example, optical character recognition technology may be used to extract at least one piece of character information in the picture. FIG. 2A is a schematic diagram illustrating a process of extracting at least one piece of character information included in a picture with optical character recognition technology.

For example, as illustrated in FIG. 2A, the process of extracting at least one piece of character information included in a picture with optical character recognition technology includes: text detection, text recognition, and result output. For example, text detection is to detect individual characters in the picture. For example, text recognition is to convert the detected text to a text format. For example, text recognition includes text feature extraction and comparison recognition; alternatively, a trained neural network (for example, a connectionist text proposal network for detecting text in a natural image or a convolutional recurrent neural network) may be used for text recognition. For example, comparison recognition is used to compare the features obtained by text feature extraction with a comparison database or a feature database (a text set containing all the text to be recognized), so that text, which is in text format and corresponding to the text in the picture, may be found based on the features of the text in the picture. For example, the specific method for text detection and text recognition using optical character recognition technology may be referred to related technologies, which will not be elaborated here. For example, the text detection may be implemented by detecting the coordinates of the upper and lower boundaries of a text row in the picture and the coordinates of the left and right boundaries of a text column in the picture. For example, CTPN (detecting text in natural image with connectionist text proposal network) and/or CRNN (convolution recurrent neural network) may be used for text recognition; OCR open source libraries (for example, Tesseract digital recognition library) may be adopted for Chinese character recognition training.

Figure 2B:
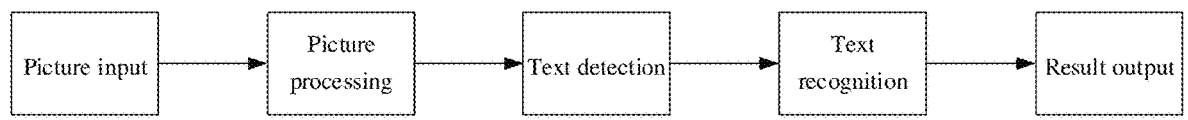
FIG. 2B is another schematic diagram illustrating a process of extracting at least one piece of character information included in a picture with optical character recognition technology.

FIG. 2B is another schematic diagram illustrating a process of extracting at least one piece of character information included in a picture with optical character recognition technology. For example, as illustrated in FIG. 2B, the process of extracting at least one piece of character information in the picture by the optical character recognition technology may further include: picture input and picture processing. For example, picture processing refers to picture preprocessing. For a specific method of picture preprocessing, reference may be made to the relevant description in step S10, and details are not described here again. For example, when the optical character recognition technology further includes image processing (for example, picture preprocessing), the picture acquired in step S10 may be a picture before picture preprocessing, and there is no need to perform additional picture preprocessing before extracting at least one piece of character information in the picture.

For example, in step S20, by checking-and-correcting (checking and then correcting if necessary) at least one piece of character information based on the knowledge graph, it can be confirmed whether the character information extracted from the picture has an error and corrects the character information having an error. Thus, it can improve the accuracy of the character information acquired by using the method for acquiring character information in a picture provided by at least one embodiment of the present disclosure.

For example, in step S20, the knowledge graph is a medical knowledge graph. For example, the medical knowledge graph may be a medical examination and test knowledge graph. For example, the medical examination and test knowledge graph may be used to provide relevant knowledge of test indicators and test reports. For example, the medical examination and test knowledge graph enables accurate identification and analysis to be possible.

Figures 3, 4:
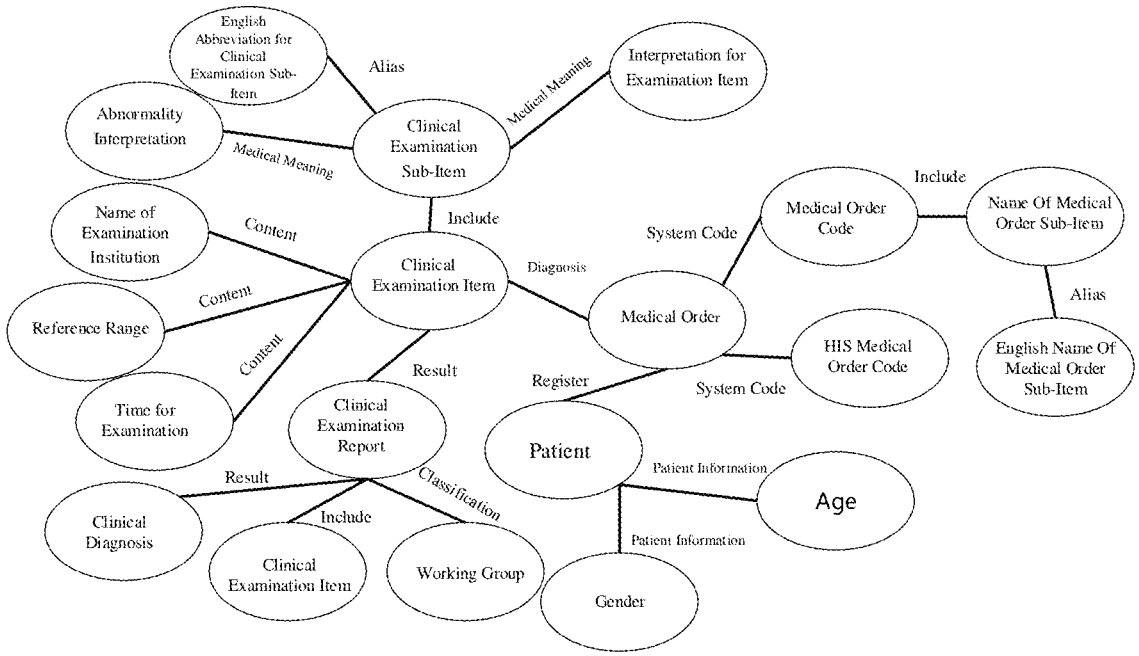
FIG. 3 is a data structure of a medical knowledge graph provided by at least one embodiment of the present disclosure.
FIG. 4 illustrates an example of a blood routine examination report.

For example, the architecture (framework or data structure) of the medical knowledge graph may adopt the data structure of the medical knowledge graph illustrated in FIG. 3. For example, a method of constructing a medical knowledge graph provided by at least one embodiment of the present disclosure may be used to construct a medical knowledge graph based on the data structure of the medical knowledge graph illustrated in FIG. 3, and the medical knowledge graph obtained through the above construction may be applied in step S20. The method for constructing a medical knowledge graph provided by at least one embodiment of the present disclosure will be described in detail in the embodiment illustrated in FIG. 12, which will not be elaborated here.

For example, the medical knowledge graph acquired based on the data structure of the medical knowledge graph illustrated in FIG. 3 may include a plurality of entities and relationships exported from a medical image archiving and communication system (picture archiving and communication system, PACS) and the laboratory information management system (LIS). For example, by making the medical knowledge graph include entities exported from the PACS system, it is possible to confirm whether the picture contains a medical image based on the medical knowledge graph, and save the medical image if the picture contains a medical image.

For example, the entities exported from the PACS system include entities that are related to medical imaging examinations and in clinical examination items, clinical examination sub-items, and clinical examination reports. For example, the entities exported from the PACS system include: electronic computer tomography images, nuclear magnetic resonance images (NMRI), ultrasound images, electrocardiograms, electroencephalograms, etc. For example, the entities exported from the LIS system include entities that are not related to medical imaging examinations and in clinical examination items, clinical examination sub-items, and clinical examination reports. For example, the entities exported from the LIS system include various laboratory examination items. For example, laboratory examination items include blood examination items, urine examination items, and stool examination items. For example, blood examination items include blood routine examination items, blood lipid examination items, blood glucose examination items, and the like. For example, blood routine examination items include the platelet count (PLT) sub-item, platelet distribution width (PDW) sub-item and plateletcrit (PCT) sub-item.

For example, the medical knowledge graph acquired based on the data structure of the medical knowledge graph illustrated in FIG. 3 may further include an entity exported from a hospital information system and/or an entity related to a sub-item description of a clinical examination sub-item. For example, the entity exported from the hospital information system include an entity related to patient information and an entity related to a medical order. For example, the entity related to the sub-item description of the clinical examination sub-item provides the description of the clinical examination sub-item and the meaning that the abnormality represents when the result of the clinical examination sub-item is abnormal, so that a patient can understand the examination result more clearly.

It should be noted that the data structure of the knowledge graph used in step S20 is not limited to the data structure of the knowledge graph illustrated in FIG. 3. For example, the data structure of the knowledge graph used in step S20 may not include the part corresponding to the hospital information system and/or the part corresponding to the medical meaning of the clinical examination sub-item in the data structure of the knowledge graph illustrated in FIG. 3.

For example, in step S20, checking-and-correcting at least one piece of character information based on the knowledge graph includes the following step S210.

Step S210: identifying character information having an error in at least one piece of character information, based on the knowledge graph.

For example, the at least one piece of character information includes a plurality of pieces of character information, and the character information having an error includes character information that is recognized incorrectly during the recognition process (for example, Chinese character "water" is incorrectly recognized as Chinese character "small") and/or character information that is not recognized during the recognition process.

For example, in step S210, identifying character information having an error in at least one piece of character information based on the knowledge graph includes the following step S211 and step 212.

Step S211: obtaining a plurality of entities respectively according to the plurality of pieces of character information in the picture, and selecting a to-be-checked-and-corrected entity from the plurality of entities for the process of determining whether the character information corresponding to the to-be-checked-and-corrected entity has an error.

FIG. 4 illustrates an example of a blood routine examination report. For example, for the picture of the blood routine examination report illustrated in FIG. 4, a plurality of entities that are obtained respectively according to the plurality of pieces of character information of the picture may include: report name, blood routine examination sub-item name (item name), and sub-item abbreviation (code), sub-item test result (result), unit of sub-item test result (unit), whether the sub-item test result is abnormal (indicated by the upward or downward arrows), and the reference value of the sub-item test result (item reference value). For example, for routine blood examination, some sub-item names and corresponding abbreviations include: platelet count (PLT), platelet distribution width (PDW) and platelet-crit (PCT).

For example, when a plurality of entities are obtained based on the plurality of pieces of character information of the picture, the plurality of entities may be checked and corrected one by one until all entities included in the plurality of pieces of character information of the picture are checked. For example, the platelet count may be selected as the to-be-checked-and-corrected entity.

Step 212, according to a hierarchical structure of the knowledge graph, determining whether the character information corresponding to the to-be-checked-and-corrected entity has an error, and, when the character information corresponding to the to-be-checked-and-corrected entity has an error, the character information corresponding to the to-be-checked-and-corrected entity is identified as character information having an error.

For example, in step 212, determining whether the character information corresponding to the to-be-checked-and-corrected entity has an error according to the hierarchical structure of the knowledge graph includes the following steps 2121 to 2124.

Step 2121: grading the plurality of entities according to the hierarchical structure of the knowledge graph.

For example, in step 2121, the plurality of entities can be graded by analyzing the structure of the table in the picture and the typesetting, size, and boldness of the text in the picture. For example, optical recognition technology can be used to determine whether a table exists in the picture, and if there is a table, further analyze (or parse) the structure of the table in the picture. For example, the specific method for analyzing a table structure can be referred to the examples illustrated in FIG. 5A and FIG. 5B, which will not be elaborated here. For example, the (relative) size of the text in the picture, whether it is bold, etc. can also be obtained by picture analysis, for example, partly using a classifier or neural network.

For example, the plurality of entities in the picture of the blood routine examination report illustrated in FIG. 4 can be graded using the following method.

First, the entity (briefly referred to as "blood routine" in the following description in the present disclosure, and this applies similarly to other entity) corresponding to the centered character string "blood routine" with a relatively large font located on the first line of the report may be taken as a first-level entity in the report; entities corresponding to "code", "item name (the name of the sub-item of the blood routine examination)", "result", "item reference value" in the first row of the table are taken as second-level entities in the report; and all the entities located in the table except for entities located in the first row of the table are taken as the third-level entities in the report.

Then, levels of entities in the report may be associated with levels of entities in the hierarchical structure of the knowledge graph. For example, it is assumed that in the hierarchical structure of the knowledge graph, "blood routine", "item name (that is, the name of the sub-item of blood routine examination)" and "platelet count" are located at the fifth, sixth, and seventh levels, respectively, "blood routine" in the picture of the blood routine examination report illustrated in FIG. 4 is at the fifth level in the hierarchical structure of the knowledge graph; "code", "item name (that is, the name of the sub-item of blood routine examination)", "result", and "item reference value" in the picture of the blood routine examination report illustrated in FIG. 4 are at the sixth level in the hierarchical structure of the knowledge graph; and "platelet count" in the picture of the blood routine examination report illustrated in FIG. 4 is at the seventh level of the hierarchical structure of the knowledge graph.

For example, based on the knowledge graph, it can be seen that the entities corresponding to such as "bed number" in the blood routine examination report do not belong to the entities related to the blood routine examination result. Therefore, the entities corresponding to such as "bed number" are ignored during the grading process performed on the plurality of entities.

Step 2122: determining a level of the to-be-checked-and-corrected entity in the hierarchical structure of the knowledge graph.

For example, in step 2122, the level of the to-be-checked-and-corrected entity in the hierarchical structure of the knowledge graph may be determined based on the grading result in step 2121. For example, when "platelet count" is selected as the to-be-checked-and-corrected entity, based on the grading result in step 2121, it may be determined that the level of the to-be-checked-and-corrected entity in the hierarchical structure of the knowledge graph is the seventh level.

Step 2123: calculating a similarity between the to-be-checked-and-corrected entity and each entity that is at the same level and has the same relationship as the to-be-checked-and-corrected entity in the knowledge graph, to obtain a plurality of entity similarities related to the to-be-checked-and-corrected entity.

For example, the similarity between the to-be-checked-and-corrected entity and each entity that is at the same level and has the same relationship as the to-be-checked-and-corrected entity in the knowledge graph is between 0 and 1.

For example, in step 2123, "having the same relationship" means that the relationship between entities that are at the same level and has the same relationship as the to-be-checked-and-corrected entity in the knowledge graph and an entity at the next higher level of the above entities is equal to the relationship between the to-be-checked-and-corrected entity and the entity at the next higher level of the to-be-checked-and-corrected entity.

For example, when "platelet count" is selected as the to-be-checked-and-corrected entity, all entities that are at the same level and have the same relationship as the to-be-checked-and-corrected entity in the knowledge graph include "platelet count", "platelet distribution width", "plateletcrit", and "percentage of neutrophils" and so on.

For example, if the "platelet count" has no error, the similarity between the to-be-checked-and-corrected entity (i.e., "platelet count") and the "platelet count" in the knowledge graph is 1; the similarities between the to-be-checked-and-corrected entity (i.e., "platelet count") and "platelet distribution width", "plateletcrit" and "percentage of neutrophils" are 0.5, 0.6 and 0, respectively.

For example, if "platelet count" is incorrectly recognized as "platelet couX", then the similarity between the to-be-checked-and-corrected entity (that is, "platelet couX") and "platelet count", "platelet distribution width", "plateletcrit" and "percentage of neutrophils" (that is, entity similarities respectively to "platelet count", "platelet distribution width", "plateletcrit" and "percentage of neutrophils"), for example, are respectively 0.8, 0.5, 0.6 and 0. It should be noted that the "X" in the "platelet couX" indicates that the character is recognized incorrectly, and the "X" in other characters or entities also has a similar meaning, which will not be repeated.

For example, in step 2123, the minimum edit distance algorithm may be used to obtain the similarity between the to-be-checked-and-corrected entity and each entity that is at the same level and has the same relationship as the to-be-checked-and-corrected entity in the knowledge graph.

Step 2124: when the maximum value of the plurality of entity similarities is smaller than a predetermined entity similarity threshold, it is determined that the to-be-checked-and-corrected entity is a to-be-checked-and-corrected entity having an error and that the character information corresponding to the to-be-checked-and-corrected entity has an error.

For example, the predetermined entity similarity threshold may be set according to actual application requirements. For example, the predetermined entity similarity threshold may be set to 1. For another example, the predetermined entity similarity threshold can also be set to 0.95. For example, when the predetermined entity similarity threshold is set to 1, as long as all entities that are at the same level and have the same relationship as the to-be-checked-and-corrected entity in the knowledge graph do not include the to-be-checked-and-corrected entity, it is determined that the to-be-checked-and-corrected entity is a to-be-checked-and-corrected entity having an error and that the character information corresponding to the to-be-checked-and-corrected entity has an error.

For example, in the case where the similarities between the to-be-checked-and-corrected entity (that is, "platelet couX") and "platelet count", "platelet distribution width", "plateletcrit", and "percentage of neutrophils" in the knowledge graph, are, for example, 0.8, 0.5, 0.6, and 0 respectively, because the maximum value (i.e., 0.8) of the plurality of entity similarities is smaller than the predetermined entity similarity threshold (for example, 1), it may be determined that the character information corresponding to the to-be-checked-and-corrected entity has an error and the to-be-checked-and-corrected entity is a to-be-checked-and-corrected entity having an error.

For example, when the maximum value of the plurality of entity similarities is larger than or equal to a predetermined entity similarity threshold, it is determined that the character information corresponding to the to-be-checked-and-corrected entity has no error.

For example, in the case where the similarities between the to-be-checked-and-corrected entity (that is, "platelet count") and "platelet count", "platelet distribution width", "plateletcrit", and "percentage of neutrophils" in the knowledge graph are respectively 1, 0.5, 0.6, and 0, because the maximum value (i.e., 1) of the plurality of entity similarities is larger than or equal to a predetermined entity similarity threshold (for example, 1), it may be determined that the character information corresponding to the to-be-checked-and-corrected entity has no error.

For example, in step S20, checking-and-correcting at least one piece of character information based on the knowledge graph further includes the following step 220.

Step S220, correcting the character information having an error based on the knowledge graph.

For example, correcting the character information having an error based on the knowledge graph includes: determining the number of all entities that are at the same level and have the same relationship as the to-be-checked-and-corrected entity in the knowledge graph, to obtain an entity number.

For example, correcting the character information having an error based on the knowledge graph also includes: when the entity number is equal to one, directly replacing the character information corresponding to the entity which has an error with character information corresponding to the entity that is at the same level and has the same relationship as the to-be-checked-and-corrected entity in the knowledge graph; alternatively, calculating a probability that an entity that is at the same level and has the same relationship as the to-be-checked-and-corrected entity is the to-be-checked-and-corrected entity having an error, to obtain an entity probability, and when the entity probability is larger than a predetermined entity probability, the character information corresponding to the to-be-checked-and-corrected entity having an error is replaced with character information corresponding to the entity that is at the same level and has the same relationship as the to-be-checked-and-corrected entity.

For example, the predetermined entity probability threshold may be set according to actual application requirements. For example, the predetermined entity probability threshold may be set to 0.5, 0.8, 0.9, or other applicable values. For example, when an entity probability for a candidate entity is smaller than or equal to the predetermined entity probability threshold, the character information having an error may be manually corrected.

For example, correcting the character information having an error based on the knowledge graph further includes: when the entity number is larger than 1, performing the following steps S221-S222.

Step S221: determining at least two candidate entities based on the plurality of entity similarities.

For example, in the step S221, determining at least two candidate entities based on the plurality of entity similarities includes: sorting all entities that are at the same level and have the same relationship as the to-be-checked-and-corrected entity in the knowledge graph based on the plurality of entity similarities in a descending order, selecting a predetermined number of entity (entities) from the top of the sequence as the at least two candidate entities; or sorting all entities that are at the same level and have the same relationship as the to-be-checked-and-corrected entity in the knowledge graph based on the plurality of entity similarities in an ascending order, and selecting a predetermined number of entity (entities) from the bottom of the sequence as the at least two candidate entities.

For example, the predetermined number may be set according to actual application requirements. For example, the predetermined number may be set to be 2, 3, 10, or other applicable numbers.

For example, in the step S221, the "platelet count", "platelet distribution width", "plateletcrit" and "percentage of neutrophils" in the knowledge graph may be sorted based on the plurality of entity similarities (i.e., 0.8, 0.5, 0.6, and 0) in a descending order as: "platelet count", "plateletcrit", "platelet distribution width" and "percentage of neutrophils". For example, when the predetermined number is set to be 2, the two entities from the top of the sequence, that is, "platelet count" and "plateletcrit" may be taken as at least two candidate entities.

For another example, in step S221, the "platelet count", "platelet distribution width", "plateletcrit" and "percentage of neutrophils" in the knowledge graph can be sorted based on the plurality of entity similarities (i.e., 0.8, 0.5, 0.6, and 0) in an ascending order as: "percentage of neutrophils", "platelet distribution width", "plateletcrit" and "platelet count". For example, when the predetermined number is set to 2, two entities from the bottom of the sequence, that is, "plateletcrit" and "platelet count" may be taken as the at least two candidate entities.

Step S222: calculating a probability that each of the at least two candidate entities is the to-be-checked-and-corrected entity having an error, to obtain a candidate probability for each of the at least two candidate entities.

For example, "the probability that each of the at least two candidate entities is the to-be-checked-and-corrected entity having an error" refers to the probability that the character information corresponding to each of the at least two candidate entities is equivalent to character information that is incorrectly recognized as the character information corresponding to the to-be-checked-and-corrected entity having an error (the right character information corresponding to the to-be-checked-and-corrected entity having an error). For example, a probability that "plateletcrit" is the to-be-checked-and-corrected entity having an error "platelet couX" refers to the probability that the character information corresponding to "plateletcrit" is equivalent to character information "platelet count" that is incorrectly recognized as the character information "platelet couX" corresponding to "platelet couX".

For example, in step S222, calculating the probability that each of the at least two candidate entities is the to-be-checked-and-corrected entity having an error includes the following steps S2221-S2223.

Step S2221: determining whether or not the to-be-checked-and-corrected entity includes a next-lower-level to-be-checked-and-corrected entity, to obtain a first determination result. The next-lower-level to-be-checked-and-corrected entity is all entities that are subordinate to the to-be-checked-and-corrected entity and at the next lower level of the to-be-checked-and-corrected entity.

For example, for a plurality of entities in the picture of the blood routine examination report illustrated in FIG. 4, when "platelet couX" is selected as the to-be-checked-and-corrected entity, it can be determined that the to-be-checked-and-corrected entity does not include a next-lower-level to-be-checked-and-corrected entity. When "item naX" is selected as the to-be-checked-and-corrected entity, it can be determined that the to-be-checked-and-corrected entity includes a next-lower-level to-be-checked-and-corrected entity, for example, the next-lower-level to-be-checked-and-corrected entity included by "item naX" includes "platelets count", "platelet distribution width", "plateletcrit" and "percentage of neutrophils" and so on.

For example, the first determination result is a first determination sub-result when it is determined that the to-be-checked-and-corrected entity includes the next-lower-level to-be-checked-and-corrected entity or a second determination sub-result when it is determined that the to-be-checked-and-corrected entity does not include the next-lower-level to-be-checked-and-corrected entity. For example, when "item naX" is selected as the to-be-checked-and-corrected entity, the first determination result is the first determination sub-result; when "platelet couX" is selected as the to-be-checked-and-corrected entity, the first determination result is the second determination sub-result.

Step S2222: determining whether or not the to-be-checked-and-corrected entity corresponds to a relevant to-be-checked-and-corrected entity to obtain a second determination result. The relevant to-be-checked-and-corrected entity is all entities that are at the same level as the to-be-checked-and-corrected entity in the hierarchical structure of the knowledge graph, related to the to-be-checked-and-corrected entity, and has a different relationship with an entity at the next higher level to which the to-be-checked-and-corrected entity is subordinate. For example, "the relevant to-be-checked-and-corrected entity is related to the to-be-checked-and-corrected entity" refers to that the relevant to-be-checked-and-corrected entity and the to-be-checked-and-corrected entity are used to describe different aspects of the same subject. For example, "platelet count (full name of the platelet count examination sub-item)" and "PLT (abbreviation of the platelet count examination sub-item)", and "100-300 (reference value of the platelet count examination sub-item)" are used to describe different aspects of the platelet count examination sub-item, and therefore, the to-be-checked-and-corrected entities "platelet count" is related to "PLT" and "100-300".

For example, for the plurality of entities of the picture of the blood routine examination report illustrated in FIG. 4, when "platelet couX" is selected as the to-be-checked-and-corrected entity, it can be determined that the to-be-checked-and-corrected entity corresponds to the relevant to-be-checked-and-corrected entity. For example, the relevant to-be-checked-and-corrected entity corresponding to "platelet couX" includes "PLT (abbreviation for platelet count)", "100-300 (reference value for platelet count)", and so on.

When "item naX" is selected as the to-be-checked-and-corrected entity, it can be determined that the to-be-checked-and-corrected entity does not correspond to the relevant to-be-checked-and-corrected entity.

For example, the second determination result is a third determination sub-result when it is determined that the to-be-checked-and-corrected entity corresponds to the relevant to-be-checked-and-corrected entity or a fourth determination sub-result when it is determined that the to-be-checked-and-corrected entity does not correspond to the relevant to-be-checked-and-corrected entity. For example, when "item naX" is selected as the to-be-checked-and-corrected entity, the second determination result is the fourth determination sub-result; when "platelet couX" is selected as the to-be-checked-and-corrected entity, the second determination result is the third determination sub-result.

Step S2223: selecting a method for calculating the probability that each of the at least two candidate entities is the to-be-checked-and-corrected entity having an error based on the first determination result and the second determination result.

For example, in step S2223, selecting a method for calculating a probability that each of the at least two candidate entities is the to-be-checked-and-corrected entity having an error based on the first determination result and the second determination result includes one of the following steps S231-step S234.

Step S232: when the first determination result is the second determination sub-result and the second determination result is the third determination sub-result, calculating a candidate probability for each of the at least two candidate entities using the relevant to-be-checked-and-corrected entity.

For example, when "platelet couX" is selected as the to-be-checked-and-corrected entity, the first determination result is the second determination sub-result, and the second determination result is the third determination sub-result (that is, "platelet couX" does not have the next-lower-level to-be-checked-and-corrected entity, but corresponding to the relevant to-be-checked-and-corrected entity), and thus the candidate probability for each of the at least two candidate entities can be calculated using the relevant to-be-checked-and-corrected entity.

For example, candidate entities for the to-be-checked-and-corrected entity (that is, "platelet couX") include "platelet count", "plateletcrit", and so on. It should be noted that, for the sake of clarity, it is assumed here that the candidate entities of the to-be-checked-and-corrected entity (that is, "platelet couX") include only "platelet count" and "plateletcrit".

For example, calculating the candidate probability for each of the at least two candidate entities using the relevant to-be-checked-and-corrected entity includes the following steps S241-S244.

Step S241: obtaining the relevant to-be-checked-and-corrected entity corresponding to the to-be-checked-and-corrected entity.

For example, the relevant to-be-checked-and-corrected entity corresponding to the to-be-checked-and-corrected entity (that is, "platelet couX") includes "PLT", "100-300", and so on.

Step S242: the following steps S2421 to S2422 are performed for each of the entities included in the relevant to-be-checked-and-corrected entity.

Step S2421: obtaining a relevant candidate entity. The relevant candidate entity is at the same level as the each of the at least two candidate entities in the hierarchical structure of the knowledge graph, is related to the each of the at least two candidate entities, and has a relationship to each of the at least two candidate entities equal to the relationship between each entity in the relevant to-be-checked-and-corrected entity and the to-be-checked-and-corrected entity.

For example, for the relevant to-be-checked-and-corrected entity "PLT", the relevant candidate entity corresponding to the candidate entity "platelet count" is "PLT", and the relevant candidate entity corresponding to the candidate entity "plateletcrit" is "PCT". For example, for the relevant to-be-checked-and-corrected entity "100-300", the relevant candidate entity corresponding to the candidate entity "platelet count" is "100-300", and the relevant candidate entity corresponding to the candidate entity "plateletcrit" is "0.17-0.35".

Step S2422: calculating a similarity between each entity included in the relevant to-be-checked-and-corrected entity and the relevant candidate entity.

For example, the similarity between the relevant to-be-checked-and-corrected entity "PLT" and the relevant candidate entity "PLT" corresponding to the candidate entity "platelet count" is 1, and the similarity between the relevant to-be-checked-and-corrected entity "PLT" and the relevant candidate entity "PCT" corresponding to the candidate entity "plateletcrit" is 0.65.

For example, the similarity between the relevant to-be-checked-and-corrected entity "100-300" and the relevant candidate entity "100-300" corresponding to the candidate entity "platelet count" is 1, and the similarity between the relevant to-be-checked-and-corrected entity "100-300" and the relevant candidate entity "0.17-0.35" corresponding to the candidate entity "plateletcrit" is 0.

Step S243: obtaining a relevant similarity for each of the at least two candidate entities based on the similarity between each entity included in the relevant to-be-checked-and-corrected entity and the relevant candidate entity.

For example, in step S243, obtaining a relevant similarity for each of the at least two candidate entities based on the similarity between each entity included in the relevant to-be-checked-and-corrected entity and the relevant candidate entity includes the following steps S2431-S2433.

Step S2431: determining an entity number of entity (entities) included in the relevant to-be-checked-and-corrected entity.

For example, when the relevant to-be-checked-and-corrected entity corresponding to the to-be-checked-and-corrected entity (that is, "platelet couX") includes only "PLT", it can be determined that the entity number of entity (entities) included in the relevant to-be-checked-and-corrected entity is 1. For another example, when the relevant to-be-checked-and-corrected entity corresponding to the to-be-checked-and-corrected entity (that is, "platelet couX") includes "PLT" and "100-300", it can be determined that the entity number of entity (entities) included in the relevant to-be-checked-and-corrected entity is 2.

Step S2432, when the entity number of entity (entities) included in the relevant to-be-checked-and-corrected entity is equal to 1, the similarity between the entity included in the relevant to-be-checked-and-corrected entity and the relevant candidate entity is taken as the relevant similarity for each of the at least two candidate entities.

For example, when the relevant to-be-checked-and-corrected entity corresponding to the to-be-checked-and-corrected entity (that is, "platelet couX") includes only "PLT", the similarity (i.e., 1) between the relevant to-be-checked-and-corrected entity "PLT" and the relevant candidate entity "PLT" corresponding to the candidate entity "platelet count"

is taken as the relevant similarity for the candidate entity "platelet count". Moreover, the similarity (i.e., 0.65) between the relevant to-be-checked-and-corrected entity "PLT" and the relevant candidate entity "PCT" corresponding to the candidate entity "plateletcrit" is taken as the relevant similarity for the candidate entity "plateletcrit".

Step S2433, when the entity number of entity (entities) included in the relevant to-be-checked-and-corrected entity is larger than 1, a weighted sum of a plurality of similarities between the entities included in the relevant to-be-checked-and-corrected entity and the relevant candidate entity is taken as the relevant similarity for each of the candidate entities.

For example, when the entity number of entity (entities) included in the relevant to-be-checked-and-corrected entity is larger than 1, a weight may be set for each entity included in the relevant to-be-checked-and-corrected entity. For example, when the relevant to-be-checked-and-corrected entity corresponding to the to-be-checked-and-corrected entity (that is, "platelet couX") includes "PLT" and "100-300", a weight of a sub-item abbreviation (for example, "PLT") may be set to 0.7, and a weight of an item reference value (for example, "100-300") may be set to 0.3.

For example, the relevant similarity for the candidate entity "platelet count"=0.7×1+0.3×1=1, that is, the relevant similarity for the candidate entity "platelet count"=0.7 (the weight of sub-item abbreviation)×1 (the similarity between the relevant to-be-checked-and-corrected entity "PLT" and the relevant candidate entity "PLT" corresponding to the candidate entity "platelet count")+0.3 (the weight of the item reference value)×1 (the similarity between the relevant to-be-checked-and-corrected entity "100-300" and the relevant candidate entity "100-300" corresponding to the candidate entity "platelet count").

For example, the relevant similarity for the candidate entity "plateletcrit"=0.7×0.65+0.3×0=0.455, that is, the relevant similarity for the candidate entity "plateletcrit"=0.7 (the weight of sub-item abbreviation)×0.65 (similarity between the relevant to-be-checked-and-corrected entity "PLT" and the relevant candidate entity "PCT" corresponding to the candidate entity "plateletcrit")+0.3(the weight of the item reference value)×0 (the similarity between the relevant to-be-checked-and-corrected entity "100-300" and the relevant candidate entity "0.17-0.35" corresponding to the candidate entity "plateletcrit").

Step S244: obtaining the candidate probability for each of the at least two candidate entities based on the relevant similarity for each of the at least two candidate entities and the entity similarity for each of the at least two candidate entities.

For example, in step S244, obtaining the candidate probability for each of the at least two candidate entities based on the relevant similarity for each of the at least two candidate entities and the entity similarity for each of the at least two candidate entities includes: taking a weighted sum of the relevant similarity for each of the at least two candidate entities and the entity similarity for each of the at least two candidate entities as the candidate probability for each of the at least two candidate entities.

For example, the candidate probability for a candidate entity=the relevant similarity for the candidate entity×the weight of the relevant similarity for the candidate entity+the entity similarity for the candidate entity×the weight of the entity similarity for the candidate entity. For example, the weights of relevant similarity and entity similarity may be set according to actual application requirements. For example, the weights of relevant similarity and entity similarity may be set to be 0.6 and 0.4, respectively.

For example, when the entity similarities of the candidate entity "platelet count" and the candidate entity "plateletcrit" are 0.8 and 0.6, respectively, and the relevant similarities of the candidate entity "platelet count" and the candidate entity "plateletcrit" are 1 and 0.455, respectively, the candidate probability for the candidate entity "platelet count"=1×0.6+0.8×0.4=0.92; the candidate probability for the candidate entity "plateletcrit"=0.455×0.6+0.6×0.4=0.513.

In some other examples, the product of the relevant similarity and the entity similarity for each of the at least two candidate entities may be used as the candidate probability for each of the at least two candidate entities. In this case, the candidate probability for the candidate entity "platelet count"=1×0.8=0.8; the candidate probability for the candidate entity "plateletcrit"=0.455×0.6=0.273.

Step S233, when the first determination result is the first determination sub-result and the second determination result is the fourth determination sub-result, calculating the candidate probability for each of the at least two candidate entities using the next-lower-level to-be-checked-and-corrected entity.

For example, when "item naX" is selected as the to-be-checked-and-corrected entity, the first determination result is the first determination sub-result; the second determination result is the fourth determination sub-result (i.e., the to-be-checked-and-corrected entity "item naX" has the next-lower-level to-be-checked-and-corrected entity, but does not correspond to the relevant to-be-checked-and-corrected entity), and the candidate probability for each of at least two candidate entities may be calculated using the next-lower-level to-be-checked-and-corrected entity. For example, the candidate entities of "item naX" include "item name" and "item reference value".

For example, calculating the candidate probability for each of the at least two candidate entities using the next-lower-level to-be-checked-and-corrected entity includes the following steps S251-S255.

Step S251: obtaining the next-lower-level to-be-checked-and-corrected entity included by the to-be-checked-and-corrected entity.

For example, the next-lower-level to-be-checked-and-corrected entity for the to-be-checked-and-corrected entity "item naX" include "platelet count", "plateletcrit", and so on. It should be noted that, for the sake of clarity, it is assumed here that the next-lower-level to-be-checked-and-corrected entity for the to-be-checked-and-corrected entity "item naX" includes only "platelet count" and "plateletcrit".

Step S252: dividing the next-lower-level to-be-checked-and-corrected entity into at least one next-lower-level to-be-checked-and-corrected entity group based on the relationship between the to-be-checked-and-corrected entity and each entity of the next-lower-level to-be-checked-and-corrected entity.

For example, because the "platelet count" and "plateletcrit" included by the next-lower-level to-be-checked-and-corrected entity for the to-be-checked-and-corrected entity "item naX" have the same relationship with the to-be-checked-and-corrected entity "item naX", here, the "platelet count" and "plateletcrit" included by the next-lower-level to-be-checked-and-corrected entity for the to-be-checked-and-corrected entity "item naX" are divided into only one next-lower-level to-be-checked-and-corrected entity group, that is, the entities included by the next-lower-level to-be-checked-and-corrected entity group are "platelet count" and "plateletcrit".

Step S253: performing the following steps S2531-S2532 for each of the at least one next-lower-level to-be-checked-and-corrected entity group.

Step S2531: obtaining a lower-level candidate entity group. The lower-level candidate entity group comprises all entities subordinate to each of the at least two candidate entities, and have a relationship with each of the at least two candidate entities equal to the relationship between each of the entities included in the next-lower-level to-be-checked-and-corrected entity group and the to-be-checked-and-corrected entity.

For example, the lower-level candidate entity group included by the candidate entity "item name" includes entities such as "platelet count", "plateletcrit", "platelet distribution width"; the lower-level candidate entity group included by the candidate entity "item reference value" includes "100-300", "0.17–0.35", "9-17" and so on.

Step S2532: calculating a similarity between each group of at least one next-lower-level to-be-checked-and-corrected entity group and the lower-level candidate entity group, to obtain at least one group similarity corresponding to the at least one next-lower-level to-be-checked-and-corrected entity group.

For example, in step S2532, obtaining at least one group similarity corresponding to the at least one next-lower-level to-be-checked-and-corrected entity group includes the following step 310.

Step 310: obtaining a maximum similarity for each of the plurality of entities included in each group of at least one next-lower-level to-be-checked-and-corrected entity group, to obtain a plurality of maximum similarities for the plurality of entities included in each group of at least one next-lower-level to-be-checked-and-corrected entity group. Here, the maximum similarity is a similarity has the maximum value among similarities between each of the plurality of entities included in each group of at least one next-lower-level to-be-checked-and-corrected entity group and all entities included in the lower-level candidate entity group.

For example, the similarities between the entity "platelet count" included in the next-lower-level to-be-checked-and-corrected entity group and all entities (for example, "platelet count", "plateletcrit", "platelet distribution width") in the lower-level candidate entity group of the candidate entity "item name" are respectively 1, 0.6 and 0.5. Therefore, the similarity having the maximum value among the similarities between the entity "platelet count" included in the next-lower-level to-be-checked-and-corrected entity group and all entities in the lower-level candidate entity group of the candidate entity "item name" is 1.

For example, the similarities between the entity "plateletcrit" included in the next-lower-level to-be-checked-and-corrected entity group and all entities (for example, "platelet count", "plateletcrit", "platelet distribution width") in the lower-level candidate entity group of the candidate entity "item name" are respectively 0.6, 1 and 0.5. Therefore, a similarity having the maximum value (that is, for the candidate entity "item name", the maximum similarity for the entity "plateletcrit" included in the next-lower-level to-be-checked-and-corrected entity group) among the similarities between the entity "plateletcrit" included in the next-lower-level to-be-checked-and-corrected entity group and all entities in the lower-level candidate entity group of the candidate entity "item name" is 1.

Therefore, for the candidate entity "item name", the plurality of maximum similarities for the plurality of entities (i.e., "platelet count" and "plateletcrit") included in the next-lower-level to-be-checked-and-corrected entity group are 1 and 1, respectively.

For example, the similarity having the maximum value (that is, for the candidate entity "item reference value", the maximum similarity for the entity "platelet count" included in the next-lower-level to-be-checked-and-corrected entity group) among the similarities between the entity "platelet count" included in the next-lower-level to-be-checked-and-corrected entity group and all entities in the lower-level candidate entity group of the candidate entity "item reference value" is 0; and the similarity having the maximum value (that is, for the candidate entity "item reference value", the maximum similarity for the entity "plateletcrit" included in the next-lower-level to-be-checked-and-corrected entity group) among the similarities between the entity "plateletcrit" included in the next-lower-level to-be-checked-and-corrected entity group and all entities in the lower-level candidate entity group of the candidate entity "item reference value" is 0. In this case, for the candidate entity "item reference value", the plurality of maximum similarities for the plurality of entities (i.e., "platelet count" and "plateletcrit") included in the next-lower-level to-be-checked-and-corrected entity group are 0 and 0, respectively.

Step 320: obtaining at least one group similarity corresponding to at least one next-lower-level to-be-checked-and-corrected entity group based on the plurality of maximum similarities.

For example, obtaining at least one group similarity corresponding to at least one next-lower-level to-be-checked-and-corrected entity group based on the plurality of maximum similarities includes: taking a weighted sum of the plurality of maximum similarities as the at least one group similarity corresponding to at least one next-lower-level to-be-checked-and-corrected entity group.

For example, the weights of the plurality of entities included in the next-lower-level to-be-checked-and-corrected entity group may be set according to actual application requirements. For example, each of the weights of the plurality of entities included in the next-lower-level to-be-checked-and-corrected entity group is equal to 1/the number of the plurality of entities. For example, each of the weights of the entities "platelet count" and "plateletcrit" in the next-lower-level to-be-checked-and-corrected entity group is equal to ½.

For example, for the candidate entity "item name", the group similarity for the next-lower-level to-be-checked-and-corrected entity group (including the entities "platelet count" and "plateletcrit")=0.5×1+0.5×1=1. For example, for the candidate entity "item reference value", the group similarity for the next-lower-level to-be-checked-and-corrected entity group (including the entities "platelet count" and "plateletcrit")=0.5×0+0.5×0=0.

Step S254: obtaining a lower-level similarity for each of the at least two candidate entities based on the at least one group similarity.

For example, in step S254, obtaining a lower-level similarity for each of the at least two candidate entities based on the at least one group similarity includes: determining a number of the next-lower-level to-be-checked-and-corrected entity groups included by the next-lower-level to-be-checked-and-corrected entity; when the number of lower-level to-be-checked-and-corrected entity groups is equal to 1, taking the group similarity for the next-lower-level to-be-checked-and-corrected entity group included by the next-lower-level to-be-checked-and-corrected entity as the lower-level similarity for each of the at least two candidate entities; and when the number of lower-level to-be-checked-and-corrected entity groups is larger than 1, taking a weighted sum of the plurality of group similarities for the next-lower-level to-be-checked-and-corrected entity groups included by the next-lower-level to-be-checked-and-corrected entity as the lower-level similarity for each of the at least two candidate entities.

For example, because the "platelet count" and "plateletcrit" included in the next-lower-level to-be-checked-and-corrected entity of the "item naX" have the same relationship with the to-be-checked-and-corrected entity "item naX", that is, the number of lower-level to-be-checked-and-corrected entity groups for the "item naX" is equal to 1. Therefore, the lower-level similarities of the candidate entity "item name" and the lower-level similarity for the candidate entity" item reference value" are 1 and 0, respectively.

Step S255: calculating the candidate probability for each of the at least two candidate entities based on the lower-level similarity and the entity similarity for each of the at least two candidate entities.

For example, in step S255, calculating the candidate probability for each of the at least two candidate entities based on the lower-level similarity and the entity similarity for each of the at least two candidate entities includes: taking a product of the lower-level similarity and the entity similarity for each of the at least two candidate entities as the candidate probability for each of the at least two candidate entities.

For example, when the entity similarities of "item name" and "item reference value" are 0.75 and 0.3, respectively, and the lower-level similarities of "item name" and "item reference value" are 1 and 0, respectively, the candidate probability for the candidate entity "item name"=0.75×1=0.75, and the candidate probability for "item reference value"=0.3×0=0.

Step S231, when the first determination result is the first determination sub-result and the second determination result is the third determination sub-result, a candidate probability for each of the at least two candidate entities is calculated using at least one of the next-lower-level to-be-checked-and-corrected entity and the relevant to-be-checked-and-corrected entity.

For example, when the first determination result is the first determination sub-result and the second determination result is the third determination sub-result, the candidate probability for each of the at least two candidate entities may be calculated using the next-lower-level to-be-checked-and-corrected entity or the candidate probability for each of the at least two candidate entities may be calculated using the relevant to-be-checked-and-corrected entity. For another example, when the first determination result is the first determination sub-result and the second determination result is the third determination sub-result, the candidate probability for each of the at least two candidate entities may be calculated using the next-lower-level to-be-checked-and-corrected entity and the relevant to-be-checked-and-corrected entity.

For example, calculating the candidate probability for each of the at least two candidate entities using the next-lower-level to-be-checked-and-corrected entity and the relevant to-be-checked-and-corrected entity includes the above steps S241-step S244 and steps S251-step S255.

For example, calculating the candidate probability for each of the at least two candidate entities using the next-lower-level to-be-checked-and-corrected entity and the relevant to-be-checked-and-corrected entity further includes: obtaining the candidate probability for each of the at least two candidate entities based on the relevant similarity, the lower-level similarity and the entity similarity for each of the at least two candidate entities.

For example, obtaining the candidate probability for each of the at least two candidate entities based on the relevant similarity, the lower-level similarity and the entity similarity for each of the at least two candidate entities includes: taking a product of the lower-level similarity and a weighted sum of the relevant similarity and the entity similarity for each of the at least two candidate entities as the candidate probability for each of the at least two candidate entities. For example, when the relevant similarity, the lower-level similarity, and the entity similarity for a candidate entity are 0.9, 1, and 0.8, respectively, the weights of the relevant similarity and the entity similarity are 0.6 and 0.4, respectively, the candidate probability of the candidate entity=(0.6×0.9+0.4×0.8)×1=0.86.

For another example, obtaining the candidate probability for each of the at least two candidate entities based on the relevant similarity, the lower-level similarity, and the entity similarity for each of the at least two candidate entities includes: taking a product of the relevant similarity, the lower-level similarity, and the entity similarity for each of the at least two candidate entities as the candidate probability for each of the at least two candidate entities. For example, when the relevant similarity, the lower-level similarity, and the entity similarity for the candidate entity are 0.9, 1, and 0.8, respectively, the candidate probability of the candidate entity=0.9×1×0.8=0.72.

Step S234, when the first determination result is the second determination sub-result and the second determination result is the fourth determination sub-result, the entity similarity for each of the at least two candidate entities is taken as a probability for each of the at least two candidate entities being the to-be-checked-and-corrected entity having an error.

For example, in step S234, if the to-be-checked-and-corrected entity has neither the next-lower-level to-be-checked-and-corrected entity nor the relevant to-be-checked-and-corrected entity, the entity similarity for each of the at least two candidate entities of the to-be-checked-and-corrected entity may be taken as the probability for each of the at least two candidate entities being the to-be-checked-and-corrected entity having an error.

For example, in step S220, correcting the character information having an error based on the knowledge graph further includes: when the entity number is larger than 1, the following step S223 is performed.

Step S223: replacing the character information corresponding to the to-be-checked-and-corrected entity having an error with the character information corresponding to the candidate entity corresponding to the maximum candidate probability.

For example, after confirming that the candidate entity "platelet count" of the to-be-checked-and-corrected entity "platelet couX" has a candidate probability of 0.8, and the candidate entity "plateletcrit" of the to-be-checked-and-corrected entity "platelet couX" has a candidate probability of 0.273, the character information corresponding to the to-be-checked-and-corrected entity "platelet couX" may be replaced with the character information corresponding to the candidate entity (i.e., "platelet count") which corresponds to the maximum candidate probability (i.e., 0.8).

For example, after confirming that the candidate entity "item name" of the to-be-checked-and-corrected entity "item naX" has a candidate probability of 0.75, and the candidate entity "item reference value" of the to-be-checked-and-corrected entity "item naX" has a candidate probability of 0, the character information corresponding to the to-be-checked-and-corrected entity "item naX" may be replaced with the character information corresponding to the candidate entity (i.e., "item name") which corresponds to the maximum candidate probability (i.e., 0.75).

Figure 5A:
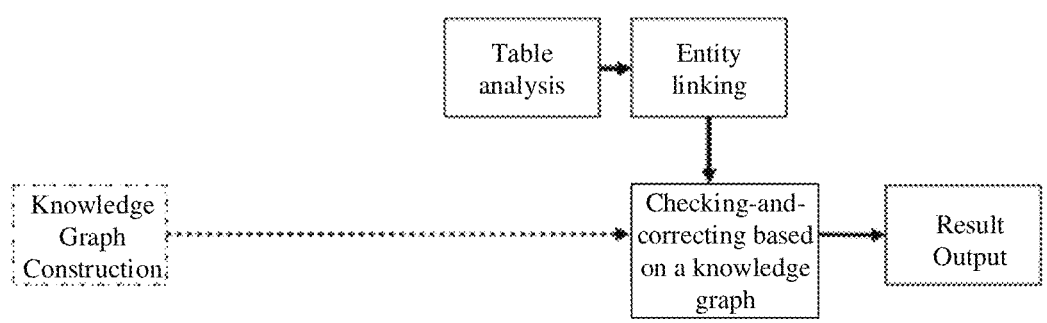
FIG. 5A is a schematic flowchart of checking-and-correcting at least one piece of character information based on a knowledge graph provided by at least one embodiment of the present disclosure.
Figure 5B:
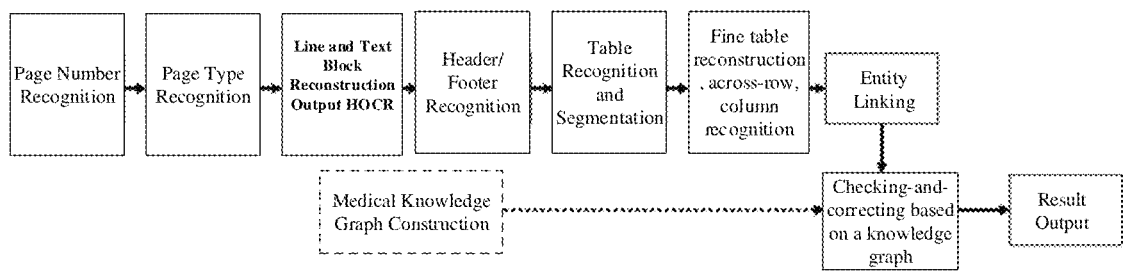
FIG. 5B is a schematic flowchart of parsing based on a knowledge graph provided by at least one embodiment of the present disclosure.

FIG. 5A is a schematic flowchart of checking-and-correcting at least one piece of character information based on a knowledge graph provided by at least one embodiment of the present disclosure. FIG. 5B is a schematic flowchart of parsing based on a knowledge graph provided by at least one embodiment of the present disclosure.

As illustrated in FIGS. 5A and 5B, the checking-and-correcting at least one piece of character information based on the knowledge graph includes table analysis (that is, table structure analysis) and entity linking (for example, entity linking can associate corresponding entities or/and entity linking can map an entity to an associated entity). For example, the result of the table analysis can be used to grade a plurality of entities included in at least one piece of character information extracted from the picture. For example, through an entity linking, the plurality of entities included in at least one piece of character information extracted from a picture can be associated with entities in the knowledge graph, so that the levels of the plurality of entities in the knowledge graph can be determined.

For example, as illustrated in FIGS. 5A and 5B, after completing the entity linking, at least one piece of character information extracted from the picture can be checked and corrected based on the knowledge graph. For example, for a specific method for checking-and-correcting at least one piece of character information extracted from a picture based on a knowledge graph, reference can be made to the method for acquiring character information in a picture provided by at least one embodiment of the present disclosure, which will not be elaborated here. For example, after checking-and-correcting of at least one piece of character information is completed, the result can be output (that is, the checked and corrected characters are output).

For example, as illustrated in FIG. 5B, table analysis may include table recognition and segmentation. For example, a program provided by OpenCV can be adopted to recognize the table, so that the table can be recognized and segmented. For example, the knowledge graph confirms that the type of the page is a table.

For example, table recognition and segmentation includes table horizontal line detection, table vertical line detection, and table vertex detection. For example, table horizontal line detection includes horizontal line detection, image binarization, and quadratic median filtering. For example, pixels of each row in the picture can be detected, and horizontal line that divides two records can be recognized through taking average adjacent pixel difference of more than 120 as a standard, so as to obtain a horizontal line list. For example, table vertical line detection includes detecting grayscale images and then performing straight line detection, with a maximum spacing of 30 pixels, a minimum line segment length of 500 pixels, and being a vertical straight line. For example, table vertex detection is used to recognize the vertexes where each cell is located.

For example, as illustrated in FIG. 5B, table analysis may also include fine table reconstruction. For example, the table fine reconstruction includes at least one of row recognition (no horizontal line), column recognition (no vertical line), and across-row recognition. For example, the row recognition can be completed after statistical and analysis of the position information (row coordinates) returned after character recognition. For example, it is possible to complete column recognition after comprehensive statistical analysis using the position information (column coordinates) returned after character recognition. For example, from the position information after row recognition (aligned upward) and column recognition (aligned leftward), using the number of rows in the column with the most rows as the maximum number of rows in the table; for the text information in the same column position and in adjacent rows, if there is no text, it is defined as across-row text, and the content is integrated into one row (when there is no information on the top and bottom, the middle is used as the basis for adjustment).

For example, as illustrated in FIG. 5B, the analysis based on the knowledge graph may further include at least one of page number recognition, page type recognition, row reconstruction and text block reconstruction, header and footer recognition, and picture/text recognition classification. For example, page number recognition is used to recognize the page number of each report using OCR, so as to determine whether the page numbers of reports form a consecutive and positive sequence, and perform adjustment to allow the page numbers of reports after adjustment to form a consecutive and positive sequence if the page numbers of reports does not form a consecutive and positive sequence. For example, an error can be reported when the page numbers of reports are not consecutive. For example, page type recognition is used to recognize whether a page comprises a medical image. For example, based on the result of layout analysis and OCR, an electronic document containing text information and layout information can be reconstructed, row reconstruction and text block reconstruction can be performed, and it can be standardized and output as HOCR (a document format adopted by OCR) format documents. For example, the header and footer recognition is used to realize the header and footer recognition of the report through a similarity recognition algorithm. For example, the similarity recognition refers to that in an examination report with a plurality of sheets, if similar text presents a plurality of times, the similar text is classified as header and footer. For example, the picture/text recognition classification includes a deep learning framework based on a general purpose, using CTPN (detecting text in natural image with connectionist text proposal network) and/or CRNN (convolution recurrent neural network), using OCR recognition open source library (for example, Tesseract digital recognition library) for Chinese character recognition training.

Figure 6A:
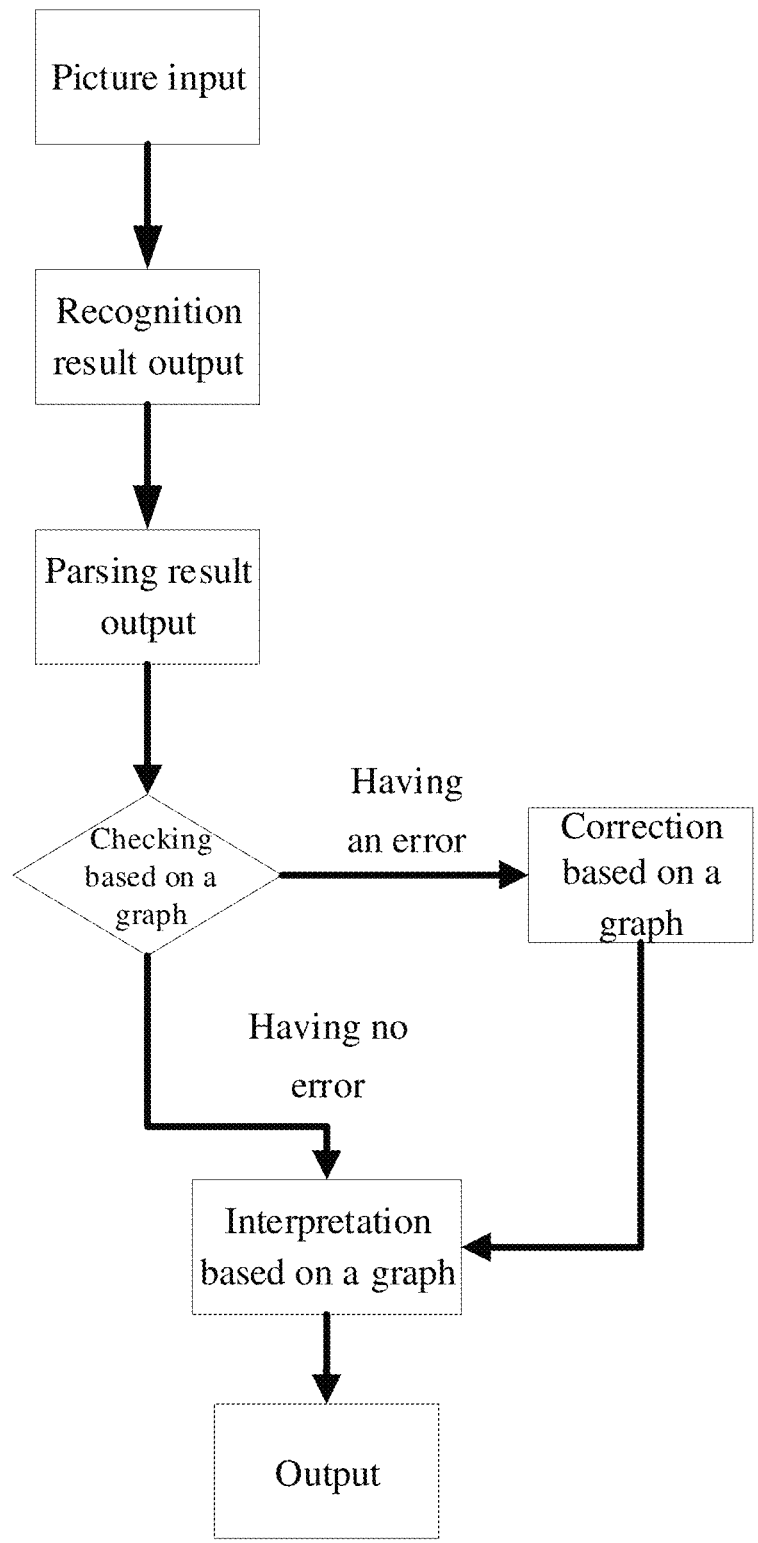
FIG. 6A is a schematic flowchart of checking-and-correcting character information in an image and adding comments based on a knowledge graph provided by at least one embodiment of the present disclosure.

FIG. 6A is a schematic flowchart of checking-and-correcting and adding explanation to character information in an image based on a knowledge graph provided by at least one embodiment of the present disclosure.

For example, as illustrated in FIG. 6A, the checking-and-correcting of character information in an image and adding of interpretation of character information in an image based on a knowledge graph provided by at least one embodiment of the present disclosure includes: picture input; recognition result output; parsing result output; and checking based on a graph.

For example, OCR can be used to extract character information from a picture and the character information can be output as a recognition result. For example, character information extracted by OCR from a picture can be used for parsing, to convert the character information in the picture to character information in text format, and the character information in text format is output as the parsing result. For example, the method may further comprise: analyzing the table in the picture, and the analysis result of the table can be used to allow the entity corresponding to the parsed character information to correspond to the entity in the knowledge graph. For example, checking based on a graph includes: using knowledge graph to check the parsing result to confirm whether the character information extracted from the picture includes character information having an error. For example, when the character information extracted from the picture does not include character information having an error, a knowledge graph can be used in a step of interpretation based on a graph, to add descriptions (e.g., sub-item descriptions) to the entities corresponding to the character information extracted from the pictures. For example, when the character information extracted from the picture includes character information having an error, the knowledge graph can be used to correct the character information having an error in a step of correction based on a graph, and then the knowledge graph is used to add a description for an entity corresponding to the corrected character information in the step of interpretation based on a graph. For example, after completing the step of interpretation based on a graph, the character information with the added description can be output.

For example, specific methods for using the knowledge graph to check the parsing result to confirm whether the character information extracted from the picture includes character information having an error, using the knowledge graph to correct the character information having an error, and using the knowledge graph to add a description to the entity corresponding to the character information, for example, may refer to the content of the method for acquiring character information in a picture and the page processing method provided by at least one embodiment of the present disclosure, which will not be elaborated here.

Figure 6B:
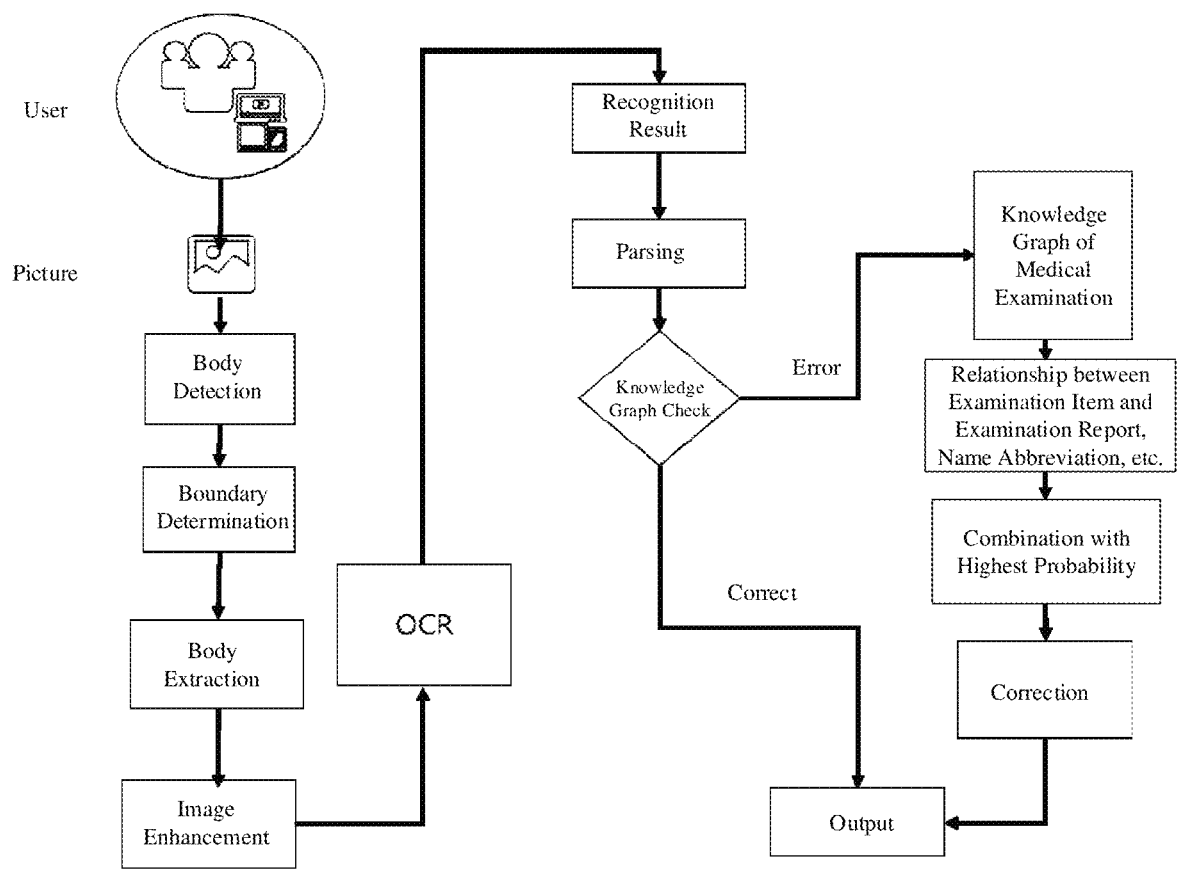
FIG. 6B is a schematic flowchart of medical document analysis based on a knowledge graph provided by at least one embodiment of the present disclosure.

FIG. 6B is a schematic flowchart of medical document analysis based on a knowledge graph provided by at least one embodiment of the present disclosure.

For example, as illustrated in FIG. 6B, the medical record analysis based on the knowledge graph includes the following steps. First, a relevant user's document (that is, medical document) is obtained, the document can be a paper or electronic file (that is, a picture); and if the document is paper, the document can be scanned to obtain a picture. For example, the medical document includes the patient's medical record, medical examination report, etc. Second, the body (body area) of the picture is detected, and thus the boundary of the body (body area) of the picture can be determined, and then the body (body area) can be extracted along the boundary of the body (body area). Third, image enhancement is performed on the body (body area) (e.g., denoising, improving contrast, etc.). Fourth, picture recognition is performed on the body area after image enhancement (that is, extraction of character information from the picture) to obtain a recognition result (that is, character information extracted from the picture). Fifth, the recognition result (that is, the character information extracted from the picture) is parsed to convert the extracted character information into a text format. Sixth, the knowledge graph (for example, general knowledge graph or medical examination and test knowledge graph) is used to check the parsed character information; if it is confirmed that the parsed character information does not have character information having an error, the parsed character information is output. If it is confirmed that the parsed character information has character information having an error, then the medical examination and test knowledge graph is used for correction, and then the corrected character information is output.

As illustrated in FIG. 6B, performing correction using the medical examination and test knowledge graph includes: confirming a combination with the highest probability based on relationship between an item to be checked (e.g., character information to be corrected) and an examination report, a name of the item to be checked and an abbreviation of the item to be checked, replacing (overwriting) character information having an error with character information corresponding to the combination with the highest probability.

For example, the information extracted from the picture may be checked and corrected based on a plurality of entities (i.e., examination report, examination item, examination sub-item, English abbreviation, medical order code, medical order name, content, diagnosis, alias, etc.) and relationship among the plurality of entities in the knowledge graph illustrated in FIG. 3. For example, a minimum edit distance algorithm may be adopted to obtain the edit distance (Levenshtein distance) of at least one of the above-mentioned entities and to-be-checked-and-corrected content (to-be-checked-and-corrected entity), so as to perform checking-and-correcting (checking and correcting) on information (e.g., character information) extracted from the image.

For example, a probability that a candidate correct content (e.g., candidate character information; e.g. "plateletcrit") corresponding to the content having an error (e.g., character information having an error, e.g., "platelet couX") is the content (e.g., "platelet count") corresponding to that the content having an error is correctly recognized can be determined by a block-based minimal-edit-distance-probability calculation method, and the content having an error can be overwritten with the candidate correct content with the largest probability. For example, the block-based minimal-edit-distance-probability calculation includes: calculating a minimal edit distance between a to-be-checked-and-corrected content (including name, abbreviation, range, etc.) and an entity (or entity and relationship) in the medical examination knowledge graph using a method of calculating by blocks, and calculating a probability based on the minimal edit distance obtained through the above calculation.

For example, block-based minimal-edit-distance-probability calculation involves the following steps. First, information is acquired through layout analysis and semantic recognition and division of tables (for example, examination institutions, clinical examination items, clinical examination sub-items, examination report, examination types, etc.); the entities corresponding to the above information are classified based on the entity names and types in the knowledge graph; after the edit distance is calculated for each entity module (for example, at least one of the entities corresponding to the above information and a corresponding knowledge graph), a content (for example, character information) corresponding to a combination with the highest probability is selected to overwrite content having an error. For example, block-based calculation refers to only calculating edit distances between entities corresponding to examination institutions and entities corresponding to examination institutions in the knowledge graph, edit distances between entities corresponding clinical examination items and entities corresponding clinical examination items in the knowledge graph, and edit distances between entities corresponding examination reports and entities corresponding examination reports in the knowledge graph. For example, the use of the block-based minimal-edit-distance-probability algorithm can make full use of the relationships between the entities in the knowledge graph (including information and included information, etc.), which can effectively reduce the calculation range of the minimum edit distance of each entity (that is, reduce the amount of calculation), improve the efficiency of error correction and the accuracy of the corrected contents.

For example, the probability can be calculated using the following formula.

$$P(B) = \sum_{i=1}^{n} P(A_i)P(B \mid A_i).$$

Here, P(B) is the probability for a correct content (for example, correct character information), and A, is at least one of entities corresponding to the examination report, examination item, examination details, word count, English abbreviation, etc. in the examination test knowledge graph.

For example, in the block-based minimal-edit-distance-probability calculation, for an entity corresponding to a surgical examination (2), calculation of edit-distance-probability only has to be performed with entities of examination items corresponding to the surgical examination (2) included in the physical examination items entities in the knowledge graph, and there is no need to perform calculation of edit distances probability with relevant entities included in physical examination institutions in the knowledge graph. For example, when calculation of edit distances probability is performed between an entity corresponding to the surgical examination (2) and an entity of an examination item corresponding to the surgical examination (2) included in the physical examination items entities in the knowledge graph, for an examination sub-item "skin color examination" included in the surgical examination (2), edit-distance calculation only has to be performed with an entity (for example, full name, English abbreviation, word count, etc.) corresponding at least one surgical examination sub-item included in the surgical examination (2) in the knowledge graph, such that correct content can be determined.

FIG. 7A is a picture corresponding to a partial blood routine examination report. FIG. 7B is a picture of the part of the blood routine examination report illustrated in FIG. 7A after being contaminated.

As illustrated in FIG. 7B, the following character information extracted from the picture corresponding to the examination report after being contaminated contains errors: "average plaXX volume", "large platelet X cases" and "lymphocyte XX ratio". It should be noted that the character information in the first column to the seventh column of FIGS. 7A and 7B respectively correspond to "sub-item serial number", "sub-item name", "sub-item abbreviation", "sub-item result", "abnormal prompt for sub-item result ",", unit for sub-item result" and "sub-item reference value".

FIG. 7C is a result of acquiring character information in a picture of FIG. 7B by using a software program based on the method for acquiring character information in a picture provided by at least one embodiment of the present disclosure. The characters in the solid line box illustrated in FIG. 7C are character information obtained from the picture illustrated in FIG. 7B, where "name" in the solid line box represents the name of the examination sub-item. As illustrated in FIG. 7C, the software program adopting the method for acquiring character information in a picture based on at least one embodiment of the present disclosure correct "average plaXX volume", "large platelet X cases", and "lymphocyte XXtage" that all have wrong character information respectively into "average platelet volume", "large platelet ratio" and "lymphocyte percentage" and output.

It should be noted that, because the characters outside the solid line frame in FIG. 7C have nothing to do with the technical solutions of the embodiments of the present disclosure, the meaning of the characters outside the solid line frame will not be elaborated here.

Figure 8:
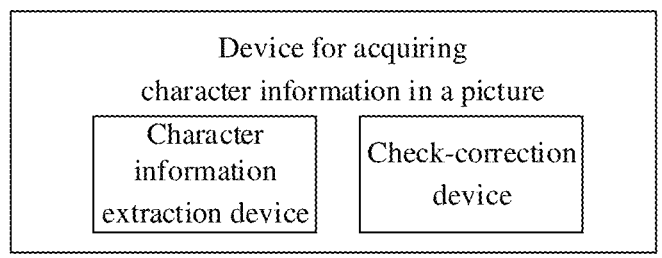
FIG. 8 illustrates a device for acquiring character information in a picture provided by at least one embodiment of the present disclosure.

At least one embodiment of the present disclosure further provides a device for acquiring character information. FIG. 8 is a device for acquiring character information in a picture provided by at least one embodiment of the present disclosure.

For example, as illustrated in FIG. 8, the device for acquiring character information in a picture includes a character information extraction device and a check-correction device.

For example, the character information extraction device is configured to acquire a picture and extract at least one piece of character information in the picture. For example, the check-correction device is configured to check and correct at least one piece of character information based on a knowledge graph.

For example, for a specific method for acquiring a picture and extracting at least one piece of character information in the picture and a specific method for checking-and-correcting at least one piece of character information based on a knowledge graph, reference can be made to the method for acquiring character information in a picture provided by at least one embodiment of the present disclosure, which will not be elaborated here.

For example, the character information extraction device and the check-correction device can be implemented by software, firmware, hardware, or any combination of software, firmware, hardware, for example, the hardware includes a field programmable gate array (FPGA), and so on.

For example, by providing a check-correction device in the device for acquiring character information in a picture, at least one piece of character information can be checked and corrected (e.g., checked and then corrected if necessary) based on the knowledge graph, such that confirming whether the character information extracted from the picture has an error can be realized and correcting the character information having an error can be realized, thereby it can improve the accuracy of character information acquired by the device for acquiring character information in pictures provided by at least one embodiment of the present disclosure.

Figure 9:
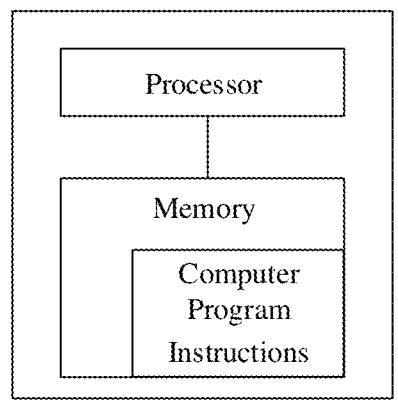
FIG. 9 illustrates another device for acquiring character information in a picture provided by at least one embodiment of the present disclosure.

At least one embodiment of the present disclosure further provides another device for acquiring character information in a picture. FIG. 9 is another device for acquiring character information in a picture provided by at least one embodiment of the present disclosure. For example, as illustrated in FIG. 9, another device for acquiring character information in a picture includes: a processor and a memory. The memory stores computer program instructions suitable to be executed by the processor. Upon the computer program instructions are executed by the processor, the processor is allowed to execute any method for acquiring character information in a picture provided by at least one embodiment of the present disclosure.

For example, the processor is, for example, a central processing unit (CPU), a graphics processor GPU, a tensor processor (TPU), or other forms of processing units with data processing capabilities and/or instruction execution capabilities. For example, the processor can be implemented as a general-purpose processor, and can also be a single chip microcomputer, a microprocessor, a digital signal processor, a dedicated image processing chip, or a field programmable logic array. For example, the memory may include at least one of volatile memory and non-volatile memory, for example, the memory may include a read-only memory (ROM), a hard disk, a flash memory, and the like. Accordingly, the memory can be implemented as one or more computer program products, and the computer program product may include various forms of computer-readable storage media, and one or more computer program instructions can be stored on the computer-readable storage media. The processor can execute the program instructions to execute any method for acquiring character information in a picture provided by at least one embodiment of the present disclosure. The memory can also store various other application programs and various data, for example, various data used and/or generated by the application programs.

For example, another device for acquiring character information in a picture provided by at least one embodiment of the present disclosure can check and correct (e.g., check and then correct if necessary) at least one piece of character information based on a knowledge graph, such that confirming whether the character information extracted from the picture has an error can be realized and correcting the character information having an error can be realized. Thus, it can improve the accuracy of character information acquired by another device for acquiring character information in a picture.

Figure 10:
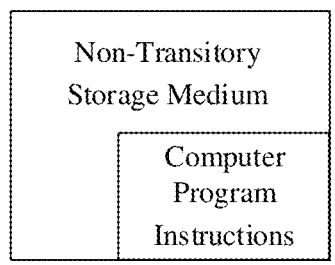
FIG. 10 illustrates a non-transitory storage medium provided by at least one embodiment of the present disclosure.

At least one embodiment of the present disclosure further provides a non-transitory storage medium. FIG. 10 is a non-transitory storage medium provided by at least one embodiment of the present disclosure. For example, as illustrated in FIG. 10, the non-transitory storage medium includes computer program instructions stored on the non-transitory storage medium. Upon the computer program instructions are executed by a processor, a computer executes any method for acquiring character information in a picture provided by at least one embodiment of the present disclosure.

For example, the non-transitory storage medium may include a magnetic storage medium, an optical storage medium, a semiconductor storage medium, etc.; for example, the non-transitory storage medium may include a read-only memory (ROM), a hard disk, a flash memory, and so on. For example, the non-transitory storage medium illustrated in FIG. 10 can be adopted to improve the accuracy of character information acquired from a picture.

Figure 11:
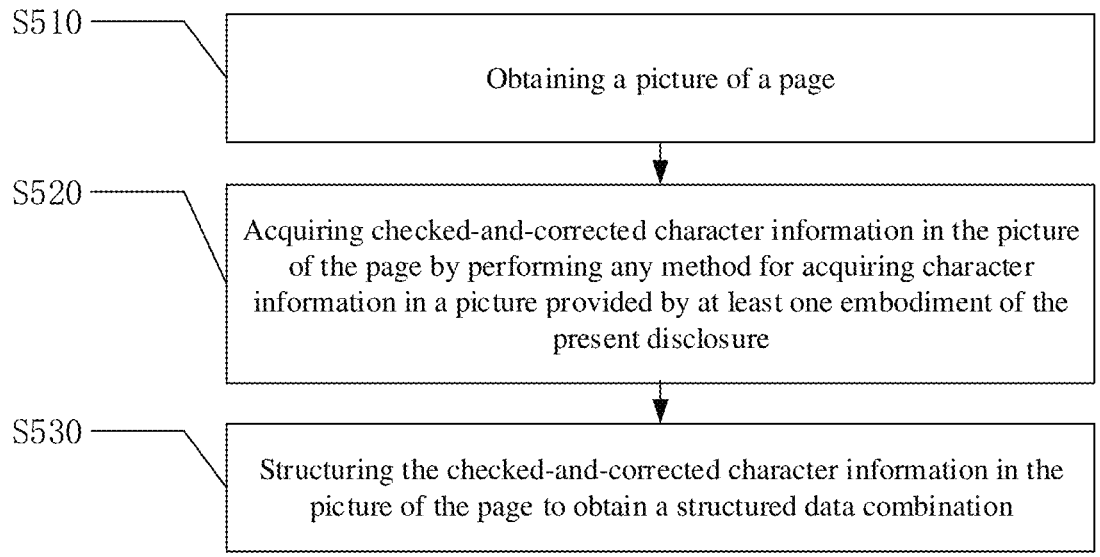
FIG. 11 is an exemplary flowchart of a page processing method provided by at least one embodiment of the present disclosure.

At least one embodiment of the present disclosure further provides a page processing method. FIG. 11 is an exemplary flowchart of a page processing method provided by at least one embodiment of the present disclosure. For example, as illustrated in FIG. 11, the page processing method includes the following steps S510-S530.

Step S510: obtaining a picture of a page.

Step S520: acquiring checked-and-corrected character information in the picture of the page by executing any method for acquiring character information provided by at least one embodiment of the present disclosure.

Step S530: structuring the checked-and-corrected character information in the picture of the page to obtain a structured data combination.

For example, in step S510, the page may be a medical examination report, a medical record, a prescription, and the like. For example, the medical examination report may include at least one of the following reports: an examination and test report, a medical examination report, a hospitalization report, a discharge report, etc.

For example, structured data is data based on a relational model, and the data based on a relational model can be stored in a relational database. For example, unstructured data is data that does not have a fixed pattern and can be stored in a non-relational database. For example, structured data can be understood by a computer, so structured data is in favor of retrieval and in favor of being displayed on a user graphical interface. Therefore, by using the page processing method provided by at least one embodiment of the present disclosure to obtain a structured data combination from a picture of a page, not only the accuracy of the character information obtained from the pictures of the page can be improved, but also patient's medical examination and test data can be utilized more effectively. For example, "platelet count"-"value"-"215" is a kind of structured data; for example, "plateletcrit"-"value"-"0.2" is also a kind of structured data. For example, a plurality pieces of structured data may be obtained based on the checked-and-corrected character information of the picture of the page, and the plurality pieces of structured data may be associated with each other to obtain a structured data combination.

For example, the page processing method may further include the following steps S540 and S550.

Step S540: confirming that the picture of the page includes a medical image based on a knowledge graph.

Step S550: adding the medical image into the structured data combination.

For example, the page processing method provided by at least one embodiment of the present disclosure can be executed in order of step S510, step S520, step S530, step S540, and step S550.

For another example, the page processing method provided by at least one embodiment of the present disclosure can be executed in order of step S510, step S520, step S540, and step S530+step S550 (that is, step S530 and step S550 are executed simultaneously).

For example, in step S540, confirming that the picture of the page includes a medical image based on a knowledge graph includes: determining that the picture of the page includes a medical image based on that the character information, that is extracted from the picture of the page and is checked and corrected based on the knowledge graph (for example, the checked-and-corrected character information obtained in step S520), includes a text corresponding to a medical image. For example, in the case where the checked-and-corrected character information obtained in step S520 includes text such as nuclear magnetic resonance image (NMRI) and does not include text corresponding to an examination sub-item (e.g., platelet count), it can be determined that the picture of the page includes a medical image, and the medical image can be extracted from the picture of the page, and thus the page processing method provided by at least one embodiment of the present disclosure can effectively save more medical examination result. For example, by making the page processing method further include the step of confirming that the picture of the page includes a medical image based on the knowledge graph, the page processing method provided by at least one embodiment of the present disclosure can also have a page type recognition function.

For example, in step S550, the medical image detected and extracted from the picture of the page can be associated with the structured data obtained in step S530, thereby the medical image can be added into an updated structured data combination.

For example, the page processing method may further include the following step S560.

Step S560: based on the knowledge graph and the plurality of entities corresponding to the checked-and-corrected character information, adding descriptions corresponding to the plurality of entities into the structured data combination.

For example, for each of the plurality of entities, based on a level in the knowledge graph where each of the plurality of entities is located, explanation for examination item (the medical meaning of the examination sub-item) and explanation for abnormality presented in the result of examination item associated with the entities (e.g., examination sub-items) corresponding to each of the plurality of entities are found in the knowledge graph, and based on the explanation for examination item and explanation for abnormality presented in the result of examination item, descriptions corresponding to plurality of entities are added in the structured data combination. Thus, it can make patients understand the meaning of the examination result better, such that the patient can use the examination result more effectively.

For example, the following descriptions can be added for the entity "platelet count": "Platelets are a type of cell in human blood, and platelet count refers to the number of platelets contained in a unit volume of blood. Low platelet count suggests aplastic anemia, Acute leukemia, radiotherapy and chemotherapy, thrombocytopenic purpura, hypersplenism, etc.; high platelet count suggests pathological myeloproliferative diseases, primary thrombocytosis, acute hemolysis, acute suppurative infections, etc.".

For example, the page processing method may further include page number recognition for combining and merging structured data located on different pages.

Figure 12:
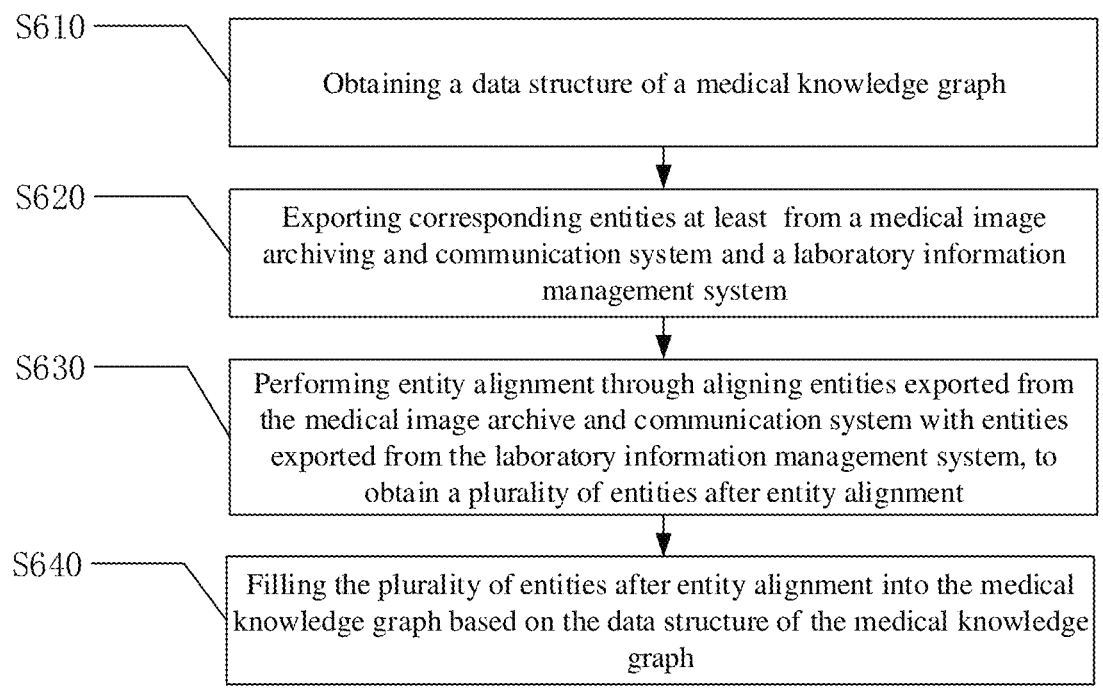
FIG. 12 is a method for constructing a medical knowledge graph provided by at least one embodiment of the present disclosure.

At least one embodiment of the present disclosure further provides a method for constructing a knowledge graph (e.g., a method for constructing a medical knowledge graph). FIG. 12 illustrates a method for constructing a medical knowledge graph provided by at least one embodiment of the present disclosure.

For example, as illustrated in FIG. 12, the method for constructing a medical knowledge graph includes the following steps S610-S640.

Step S610: obtaining a data structure of a medical knowledge graph.

For example, in step S610, the data structure of the medical knowledge graph may adopt the data structure of the medical knowledge graph illustrated in FIG. 3, but the embodiments of the present disclosure are not limited thereto. For example, the data structure of the medical knowledge graph may not include the part corresponding to the hospital information system and/or the part corresponding to the medical meaning of the clinical examination sub-item in the data structure of the medical knowledge graph illustrated in FIG. 3. For example, the data structure (framework for the medical knowledge graph) for constructing a medical knowledge graph includes defining types of entities and types of relationships between entities.

Step S620: exporting corresponding entities at least from a medical image archiving and communication system and a laboratory information management system.

For example, the corresponding entities may be manually exported from the medical image archiving and communication system and the laboratory information management system. For another example, the export function of the medical image archiving and communication system and the laboratory information management system may be used to automatically export the corresponding entities from the medical image archiving and communication system and the laboratory information management system.

For example, by making the medical knowledge graph include entities corresponding to a medical image archiving and communication (PACS) system, it is possible to confirm whether the picture comprises a medical image, and to extract the medical image from the picture of the page if the picture comprises a medical image. Thus, the knowledge graph obtained based on the method for constructing the medical knowledge graph provided by at least one embodiment of the present disclosure can be used to effectively save more medical examination result.

Step S630: performing entity alignment through aligning entities exported from the medical image archive and communication system with entities exported from the laboratory information management system, to obtain a plurality of entities after entity alignment.

For example, entity alignment is performed, through aligning the entities exported from the medical image archiving and communication system with the entities exported from the laboratory information management system, to associate an entity exported from the medical image archiving and communication system and an entity that is exported from the laboratory information management system and is substantially the same (has the same meaning) as the entity exported from the medical image archiving and communication system. For example, the medical image archiving and communication system may use "abbreviations" to represent "abbreviations of item names", while the laboratory information management system may use "codes" to represent "abbreviations of item names". In this case, in step S630, both of the "abbreviations" and "codes" can be associated with the "abbreviations of item names" (or directly associate the "abbreviations" and "code"), so that entity alignment is achieved for the entities exported from the medical image archiving and communication system and the entities exported from the laboratory information management system.

For example, by performing entity alignment through aligning the entities exported from the medical image archiving and communication system with the entities exported from the laboratory information management system, the knowledge graph acquired based on the method for constructing the medical knowledge graph provided by at least one embodiment of the present disclosure can have wider applicability.

For example, in addition to the entity alignment on the entities exported from the medical image archiving and communication system and the entities exported from the laboratory information management system, it is also possible to perform other processing on the entities exported from the medical image archiving and communication system and the entities exported from the laboratory information management system in combination with medical literature, guides, papers, etc. For example, other processing includes data cleansing (e.g., removing irrelevant entities) and data supplementation (for supplementing important entities that have not been included in the above two systems).

Step S640: filling the plurality of entities after entity alignment into the medical knowledge graph based on the data structure of the medical knowledge graph.

For example, when entity alignment and other processing are performed for entities exported from the medical image archiving and communication system and entities exported from the laboratory information management system, the entities after the entity alignment and other processing are completed can be filled into the medical knowledge graph based on the data structure of the medical knowledge graph.

For example, the method for constructing the medical knowledge graph includes: exporting corresponding entities from a hospital information system; in this case, entity alignment may be performed through aligning the entities exported from the hospital information system with the entities after the entity alignment; and the entities exported from the hospital information system and aligned with the entities after the entity alignment may be filled into the medical knowledge graph based on the data structure of the medical knowledge graph.

For example, when corresponding entities need to be exported from the hospital information system, the corresponding entities may be exported from the hospital information system in step S620, and in step S630, entity alignment is performed on all of the entities exported from the hospital information system, the entities exported from the medical image archiving and communication system and the entities exported from the laboratory information management system.

For example, the method for constructing the medical knowledge graph further includes: obtaining sub-item descriptions for clinical examination sub-items related to a laboratory information management system; processing the sub-item descriptions and filling the processed sub-item descriptions into the medical knowledge graph.

For example, the sub-item descriptions, recorded on the Internet, for the clinical examination sub-item related to the laboratory information management system may be obtained by a crawler (that is, a web robot). For example, a sub-item description may include "Low hematocrit, commonly seen in patients with anemia and when the patient's blood is thinned."

For example, processing of the acquired sub-item descriptions of the clinical examination sub-items includes cleaning (i.e., removing irrelevant information). For another example, processing of the acquired sub-item descriptions for the clinical examination sub-items may include: merging (that is, merging descriptions obtained from a plurality of information sources) and cleaning (that is, removing irrelevant or redundant information).

For example, by processing the sub-item descriptions and filling the processed sub-item descriptions into the medical knowledge graph, a method and a device utilizing the knowledge graph obtained by the method for constructing the medical knowledge graph provided by at least one embodiment of the present disclosure has the potential to present to patients a description of the clinical examination sub-item and the meaning of abnormality when the result of a clinical examination sub-item is abnormal, so as to allow patients to understand the meaning of examination results more clearly, and allows patients to use examination results more effectively.

Figure 13:
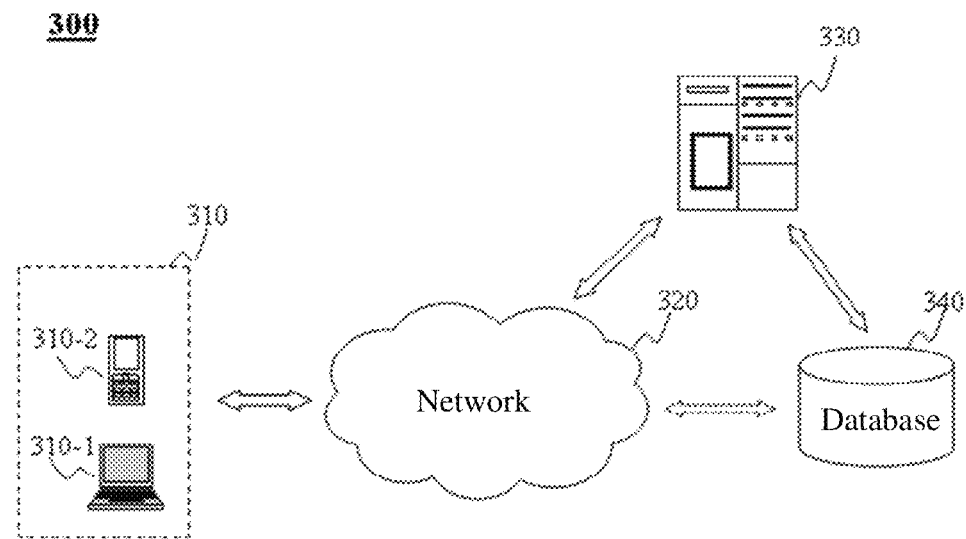
FIG. 13 is a diagram illustrates an exemplary scenario of a system for acquiring character information in a picture provided by at least one embodiment of the present disclosure.

FIG. 13 illustrates an exemplary scene diagram of a system for acquiring character information in a picture provided by at least one embodiment of the present disclosure. As illustrated in FIG. 13, the system 300 for acquiring character information in a picture may include a user terminal 310, a network 320, a server 330, and a database 340.

For example, the user terminal 310 may be a computer 310-1 and a portable terminal 310-2 illustrated in FIG. 13. It can be understood that the user terminal may also be any other type of electronic devices capable of performing data reception, processing, and display, and the user terminal 310 may include but not limited to a desktop computer, a laptop computer, a tablet computer, a smart home device, a wearable device, a car electronic equipment, a medical electronic equipment, etc.

For example, the network 320 may be a single network, or a combination of at least two different networks. For example, the network 320 may include, but is not limited to, one or a combination of a plurality of types of local area networks, wide area networks, public networks, private networks, the Internet, mobile communication networks, and the like.

For example, the server 330 may be implemented as a single server or a server group, and the servers in the server group are connected through a wired network or a wireless network. The wired network may realize communication through transmission of twisted pair, coaxial cable, or optical fiber, for example, and the wireless network may adopt, for example, 3G/4G/5G mobile communication network, Bluetooth, Zigbee, or WiFi. The present disclosure does not limit the types and functions of the network. The one server group may be centralized, such as a data center, or distributed. The server may be local or remote. For example, the server 330 may be a general-purpose server or a dedicated server, and may be a virtual server or a cloud server.

For example, the database 340 may be used to store various data utilized, generated, and output from the operation of the user terminal 310 and the server 330. The database 340 may be connected or communicated with the server 330 or a part of the server 330 via the network 320, or directly connected or communicated with the server 330, or may be connected or communicated with the server 330 via a combination of the above two methods. In some embodiments, the database 340 may be an independent device. In other embodiments, the database 340 may also be integrated in at least one of the user terminal 310 and the server 340. For example, the database 340 may be installed on the user terminal 310 or the server 340. For another example, the database 340 may also be distributed, a part of the database 340 is set on the user terminal 310, and another part of the database 340 is set on the server 340.

In an example, the user terminal 310 may acquire a picture (for example, a picture obtained through taking a picture of a paper medical examination report using a camera of the user terminal), and send the acquired picture via the network 320 or other technologies (for example, Bluetooth communication, infrared communication, etc.) to the server 330. The server 330 may obtain the information of the knowledge graph from the database, and execute the method for acquiring character information in a picture and the page processing method provided by at least one embodiment of the present disclosure, to obtain checked-and-corrected character information extracted from the picture and the structured data combination obtained by structuring the checked-and-corrected character information. Then, the server 330 may store the structured data combination in the database 340 and send the structured data combination to the user terminal 310. Finally, the user terminal displays (for example, through a pre-designed graphical user interface) the above structured data combination.

In some implementations, the server 330 may use an application program built in the server to execute the method for acquiring character information in a picture and the page processing method provided by at least one embodiment of the present disclosure. In some other implementation, the server 330 may execute the method for acquiring the character information in the picture and the page processing method provided by at least one embodiment of the present disclosure by calling an application program stored outside the server.

In another example, the user terminal 310 may acquire a picture (for example, a picture obtained through taking a picture of a paper medical test report by using a camera of the user terminal), extract character information from the picture, and send the extracted character information via the network 320 or other technology (for example, Bluetooth communication, infrared communication, etc.) to the server 330. The server 330 may acquire the information of the knowledge graph from the database, and perform the method for acquiring the character information in the picture and the page processing method provided by at least one embodiment of the present disclosure for checking-and-correcting the received character information and structuring the checked-and-corrected character information to obtain a structured data combination. Then, the server 330 may store the structured data combination in the database 340 and send the structured data combination to the user terminal 310. Finally, the user terminal displays (for example, through a pre-designed graphical user interface) the above structured data combination. In some implementations, the user terminal may use a built-in application program of the user terminal to extract character information in the picture. In other implementation, the user terminal may extract the character information in the picture by calling an application program stored externally of the user terminal.

Figure 14:
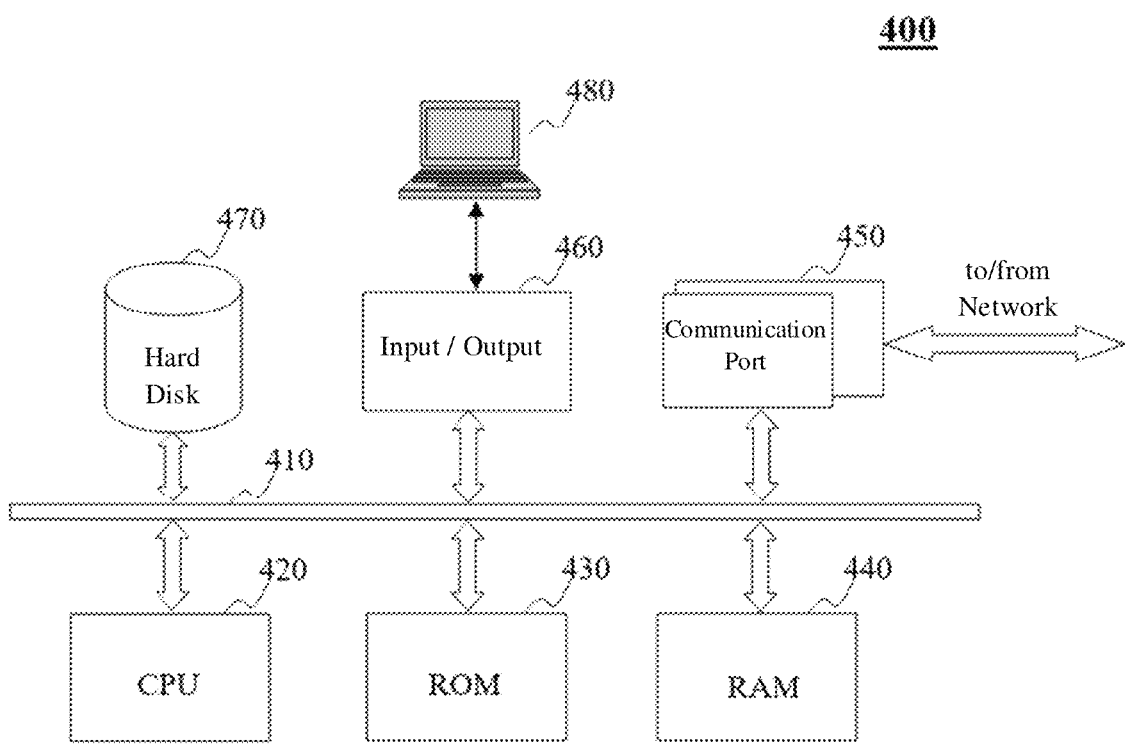
FIG. 14 illustrates a computing device provided by at least one embodiment.

The method, the device, or the system according to the embodiments of the present application may also be implemented by the architecture of a computing device 400 illustrated in FIG. 14.

FIG. 14 illustrates architecture of a computing device 400. As illustrated in FIG. 14, the computing device 400 may include a bus 410, one or at least two CPUs 420, a read only memory (ROM) 430, a random access memory (RAM) 440, a communication port 450 connected to a network, an input/output component 460, a hard disk 470, etc. The storage device (for example, the ROM 430 or the hard disk 470) in the computing device 400 may store instructions corresponding to at least one of a method for acquiring character information in a picture, a page processing method, and a method for constructing a medical knowledge map provided by at least one embodiment of the present disclosure and store various related data or files. The computing device 400 may also include a human-machine user interface 480. Of course, the architecture illustrated in FIG. 14 is only exemplary. When implementing different devices, one or at least two components in the computing device illustrated in FIG. 14 may be omitted according to actual needs.

Although detailed description has been given above to the present disclosure with general description and embodiments, it shall be apparent to those skilled in the art that some modifications or improvements may be made on the basis of the embodiments of the present disclosure. Therefore, all the modifications or improvements made without departing from the spirit of the present disclosure shall all fall within the scope of protection of the present disclosure.

What are described above is related to the illustrative embodiments of the disclosure only and not limitative to the scope of the disclosure; the scopes of the disclosure are defined by the accompanying claims.

What is claimed is:

1. A method for acquiring character information in a picture, comprising:
   acquiring a picture and extracting at least one piece of character information in the picture; and
   checking-and-correcting the at least one piece of character information based on a knowledge graph,
   wherein the checking-and-correcting the at least one piece of character information based on a knowledge graph comprises:
      identifying character information having an error in the at least one piece of character information based on the knowledge graph; and
      correcting the character information having an error based on the knowledge graph,
   wherein the at least one piece of character information comprises a plurality of pieces of character information; and
   the identifying character information having an error in the at least one piece of character information based on the knowledge graph comprises:
      obtaining a plurality of entities respectively based on the plurality of pieces of character information in the picture, and selecting an entity from the plurality of entities as a to-be-checked-and-corrected entity for a process of determining whether character information corresponding to the to-be-checked-and-corrected entity has an error; and
      determining whether the character information corresponding to the to-be-checked-and-corrected entity has an error according to a hierarchical structure of the knowledge graph, and identifying the character information corresponding to the to-be-checked-and-corrected entity as the character information having an error when the character information corresponding to the to-be-checked-and-corrected entity has an error,
   wherein the determining whether the character information corresponding to the to-be-checked-and-corrected entity has an error according to a hierarchical structure of the knowledge graph comprises:
      grading the plurality of entities according to the hierarchical structure of the knowledge graph;
      determining a level of the to-be-checked-and-corrected entity in the hierarchical structure of the knowledge graph;
      calculating a similarity between the to-be-checked-and-corrected entity and each entity that is at a same level and has a same relationship as the to-be-checked-and-corrected entity in the knowledge graph, to obtain a plurality of entity similarities related to the to-be-checked-and-corrected entity; and
      when a maximum value of the plurality of entity similarities is smaller than a predetermined entity similarity threshold, determining that the to-be-checked-and-corrected entity is a to-be-checked-and-corrected entity having an error and that the character information corresponding to the to-be-checked-and-corrected entity has an error.

2. The method for acquiring character information according to claim 1, wherein the correcting the character information having an error based on the knowledge graph comprises:
   determining a number of all entities that are at the same level and have the same relationship as the to-be-checked-and-corrected entity in the knowledge graph, to obtain an entity number;
   when the entity number is equal to 1,
      directly replacing character information corresponding to the to-be-checked-and-corrected entity having an error with character information corresponding to the entity that is at the same level and has the same relationship as the to-be-checked-and-corrected entity in the knowledge graph, or
      calculating a probability that the entity that is at the same level and has the same relationship as the to-be-checked-and-corrected entity is the to-bechecked-and-corrected entity having an error, to obtain an entity probability, and when the entity probability is larger than a predetermined entity probability, replacing character information corresponding to the to-be-checked-and-corrected entity having an error with character information corresponding to the entity that is at the same level and has the same relationship as the to-be-checked-and-corrected entity; and when the entity number is larger than 1, performing a following method comprising:
 determining at least two candidate entities based on the plurality of entity similarities;
 calculating a probability that each of the at least two candidate entities is the to-be-checked-and-corrected entity having an error, to obtain a candidate probability for the each of the at least two candidate entities; and
 replacing character information corresponding to the to-be-checked-and-corrected entity having an error with character information corresponding to a candidate entity corresponding to a maximum candidate probability.

3. The method for acquiring character information according to claim 2, wherein the determining at least two candidate entities based on the plurality of entity similarities comprises:
 sorting all entities that are at the same level and have the same relationship as the to-be-checked-and-corrected entity in the knowledge graph based on the plurality of entity similarities in a descending order to obtain a sequence, selecting a predetermined number of entities at a beginning of the sequence as the at least two candidate entities; or
 sorting all entities that are at the same level and have the same relationship as the to-be-checked-and-corrected entity in the knowledge graph based on the plurality of entity similarities in an ascending order to obtain a sequence, and selecting a predetermined number of entities at an end of the sequence as the at least two candidate entities.

4. The method for acquiring character information according to claim 2, wherein the calculating a probability that each of the at least two candidate entities is the to-be-checked-and-corrected entity having an error comprises:
 determining whether the to-be-checked-and-corrected entity comprises a next-lower-level to-be-checked-and-corrected entity, to obtain a first determination result, wherein the next-lower-level to-be-checked-and-corrected entity is all entities that are subordinate to the to-be-checked-and-corrected entity and at a next lower level of the to-be-checked-and-corrected entity;
 determining whether the to-be-checked-and-corrected entity corresponds to a relevant to-be-checked-and-corrected entity, to obtain a second determination result, wherein the relevant to-be-checked-and-corrected entity is all entities, that are at the same level as the to-be-checked-and-corrected entity in the hierarchical structure of the knowledge graph, related to the to-be-checked-and-corrected entity, and have a different relationship with an entity at a next higher level to which the to-be-checked-and-corrected entity is subordinate; and
 selecting a method for calculating the probability that the each of the at least two candidate entities is the to-be-checked-and-corrected entity having an error, based on the first determination result and the second determination result;

the first determination result is a first determination sub-result when determining that the to-be-checked-and-corrected entity comprises the next-lower-level to-be-checked-and-corrected entity, or a second determination sub-result when determining that the to-be-checked-and-corrected entity does not comprise the next-lower-level to-be-checked-and-corrected entity; and the second determination result is a third determination sub-result when determining that the to-be-checked-and-corrected entity corresponds to the relevant to-be-checked-and-corrected entity or a fourth determination sub-result when determining that the to-be-checked-and-corrected entity does not correspond to the relevant to-be-checked-and-corrected entity.

5. The method for acquiring character information according to claim 4, wherein the selecting a method for calculating the probability that the each of the at least two candidate entities is the to-be-checked-and-corrected entity having an error, based on the first determination result and the second determination result comprises:
 when the first determination result is the first determination sub-result and the second determination result is the third determination sub-result, calculating the candidate probability for the each of the at least two candidate entities using at least one of the next-lower-level to-be-checked-and-corrected entity and the relevant to-be-checked-and-corrected entity;
 when the first determination result is the second determination sub-result and the second determination result is the third determination sub-result, calculating the candidate probability for the each of the at least two candidate entities using the relevant to-be-checked-and-corrected entity;
 when the first determination result is the first determination sub-result and the second determination result is the fourth determination sub-result, calculating the candidate probability for the each of the at least two candidate entities using the next-lower-level to-be-checked-and-corrected entity; and
 when the first determination result is the second determination sub-result and the second determination result is the fourth determination sub-result, taking the entity similarity for the each of the at least two candidate entities as the probability for the each of the at least two candidate entities being the to-be-checked-and-corrected entity having an error.

6. The method for acquiring character information according to claim 5, wherein the calculating the candidate probability for the each of the at least two candidate entities using the relevant to-be-checked-and-corrected entity comprises:
 obtaining the relevant to-be-checked-and-corrected entity corresponding to the to-be-checked-and-corrected entity;
 for each entity in the relevant to-be-checked-and-corrected entity, performing a method comprising:
 obtaining a relevant candidate entity, wherein the relevant candidate entity is at a same level as the each of the at least two candidate entities in the hierarchical structure of the knowledge graph, is related to the each of the at least two candidate entities, and has a relationship to the each of the at least two candidate entities equal to a relationship between the each entity in the relevant to-be-checked-and-corrected entity and the to-be-checked-and-corrected entity, and calculating a similarity between the each entity in the relevant to-be-checked-and-corrected entity and the relevant candidate entity;

obtaining a relevant similarity for the each of the at least two candidate entities based on the similarity between the each entity in the relevant to-be-checked-and-corrected entity and the relevant candidate entity; and obtaining the candidate probability for the each of the at least two candidate entities based on the relevant similarity and the entity similarity for the each of the at least two candidate entities.

7. The method for acquiring character information according to claim 6, wherein the obtaining a relevant similarity for the each of the at least two candidate entities based on the similarity between the each entity in the relevant to-be-checked-and-corrected entity and the relevant candidate entity comprises:

determining an entity number of entities in the relevant to-be-checked-and-corrected entity; when the entity number of entities in the relevant to-be-checked-and-corrected entity is equal to 1, taking the similarity between the each entity in the relevant to-be-checked-and-corrected entity and the relevant candidate entity as the relevant similarity for the each of the at least two candidate entities;

when the entity number of entities in the relevant to-be-checked-and-corrected entity is larger than 1, taking a weighted sum of a plurality of similarities between the entities in the relevant to-be-checked-and-corrected entity and the relevant candidate entity as the relevant similarity for the each of the at least two candidate entities; and the obtaining the candidate probability for the each of the at least two candidate entities based on the relevant similarity and the entity similarity for the each of the at least two candidate entities comprises: taking a weighted sum of the relevant similarity and the entity similarity for the each of the at least two candidate entities as the candidate probability for the each of the at least two candidate entities.

8. The method for acquiring character information according to claim 5, wherein the calculating the candidate probability for the each of the at least two candidate entities using the next-lower-level to-be-checked-and-corrected entity comprises:

obtaining the lower-level to-be-checked-and-corrected entity comprised by the to-be-checked-and-corrected entity;

dividing the next-lower-level to-be-checked-and-corrected entity into at least one next-lower-level to-be-checked-and-corrected entity group based on a relationship between the to-be-checked-and-corrected entity and each entity of the next-lower-level to-be-checked-and-corrected entity;

for each of the at least one next-lower-level to-be-checked-and-corrected entity group, performing a method comprising:

obtaining a lower-level candidate entity group, wherein the lower-level candidate entity group comprises all entities subordinate to the each of the at least two candidate entities, and have a relationship with the each of the at least two candidate entities equal to a relationship between each of the entities in the next-lower-level to-be-checked-and-corrected entity group and the to-be-checked-and-corrected entity, calculating a similarity between each group of the at least one next-lower-level to-be-checked-and-corrected entity group and the lower-level candidate entity group, to obtain at least one group similarity corresponding to the at least one next-lower-level to-be-checked-and-corrected entity group;

obtaining a lower-level similarity for the each of the at least two candidate entities based on the at least one group similarity; and calculating the candidate probability for the each of the at least two candidate entities based on the lower-level similarity and the entity similarity for the each of the at least two candidate entities.

9. The method for acquiring character information according to claim 8, wherein obtaining at least one group similarity corresponding to the at least one next-lower-level to-be-checked-and-corrected entity group comprises:

obtaining a maximum similarity for each of the plurality of entities in the each group of the at least one next-lower-level to-be-checked-and-corrected entity group, to obtain a plurality of maximum similarities for the plurality of entities in the each group of the at least one next-lower-level to-be-checked-and-corrected entity group, wherein the maximum similarity is a similarity has a maximum value among similarities between the each of the plurality of entities in the each group of the at least one next-lower-level to-be-checked-and-corrected entity group and all entities in the lower-level candidate entity group, and obtaining at least one group similarity corresponding to the at least one next-lower-level to-be-checked-and-corrected entity group based on the plurality of maximum similarities; and the obtaining at least one group similarity corresponding to the at least one next-lower-level to-be-checked-and-corrected entity group based on the plurality of maximum similarities comprises: taking a weighted sum of the plurality of maximum similarities as the at least one group similarity corresponding to the at least one next-lower-level to-be-checked-and-corrected entity group.

10. The method for acquiring character information according to claim 8, wherein the obtaining a lower-level similarity for the each of the at least two candidate entities based on the at least one group similarity comprises:

determining a number of the next-lower-level to-be-checked-and-corrected entity groups comprised by the next-lower-level to-be-checked-and-corrected entity, when the number of lower-level to-be-checked-and-corrected entity groups is equal to 1, taking the group similarity for the next-lower-level to-be-checked-and-corrected entity group comprised by the next-lower-level to-be-checked-and-corrected entity as the lower-level similarity for the each of the at least two candidate entities;

when the number of lower-level to-be-checked-and-corrected entity groups is larger than 1, taking a weighted sum of a plurality of group similarities for the next-lower-level to-be-checked-and-corrected entity groups comprised by the next-lower-level to-be-checked-and-corrected entity as the lower-level similarity for each of the at least two candidate entities;

the calculating the candidate probability for the each of the at least two candidate entities based on the lower-level similarity and the entity similarity for the each of the at least two candidate entities comprises: taking a product of the lower-level similarity and the entity similarity for the each of the at least two candidate entities as the candidate probability for the each of the at least two candidate entities.

11. A page processing method, comprising:
obtaining a picture of a page; and
acquiring checked-and-corrected character information in the picture of the page by performing the method for acquiring character information according to claim 1; and
structuring the checked-and-corrected character information in the picture of the page to obtain a structured data combination.

12. The page processing method according to claim 11, further comprising:
confirming that the picture of the page comprises a medical image based on a knowledge graph; and
adding the medical image to the structured data combination.

13. The page processing method according to claim 11, further comprising:
based on the knowledge graph and a plurality of entities corresponding to the checked-and-corrected character information, adding descriptions corresponding to the plurality of entities to the structured data combination.

14. A device for acquiring character information in a picture, comprising: a character information extraction device and a check-correction device,
wherein the character information extraction device is configured to acquire a picture and extract at least one piece of character information in the picture; and
the check-correction device is configured to check and correct at least one piece of character information based on a knowledge graph,
wherein the checking-and-correcting the at least one piece of character information based on a knowledge graph comprises:
identifying character information having an error in the at least one piece of character information based on the knowledge graph; and
correcting the character information having an error based on the knowledge graph,
wherein the at least one piece of character information comprises a plurality of pieces of character information; and
the identifying character information having an error in the at least one piece of character information based on the knowledge graph comprises:
obtaining a plurality of entities respectively based on the plurality of pieces of character information in the picture, and selecting an entity from the plurality of entities as a to-be-checked-and-corrected entity for a process of determining whether character information corresponding to the to-be-checked-and-corrected entity has an error; and
determining whether the character information corresponding to the to-be-checked-and-corrected entity has an error according to a hierarchical structure of the knowledge graph, and identifying the character information corresponding to the to-be-checked-and-corrected entity as the character information having an error when the character information corresponding to the to-be-checked-and-corrected entity has an error,
wherein the determining whether the character information corresponding to the to-be-checked-and-corrected entity has an error according to a hierarchical structure of the knowledge graph comprises:
grading the plurality of entities according to the hierarchical structure of the knowledge graph;
determining a level of the to-be-checked-and-corrected entity in the hierarchical structure of the knowledge graph;
calculating a similarity between the to-be-checked-and-corrected entity and each entity that is at a same level and has a same relationship as the to-be-checked-and-corrected entity in the knowledge graph, to obtain a plurality of entity similarities related to the to-be-checked-and-corrected entity; and
when a maximum value of the plurality of entity similarities is smaller than a predetermined entity similarity threshold, determining that the to-be-checked-and-corrected entity is a to-be-checked-and-corrected entity having an error and that the character information corresponding to the to-be-checked-and-corrected entity has an error.

15. A non-transitory storage medium, comprising computer program instructions stored on the non-transitory storage medium,
wherein when the computer program instructions are executed by a processor, a computer executes the method for acquiring character information according to claim 1.

* * * * *